US006852353B2

(12) United States Patent
Qiu et al.

(10) Patent No.: US 6,852,353 B2
(45) Date of Patent: Feb. 8, 2005

(54) PROCESS FOR SURFACE MODIFYING SUBSTRATES AND MODIFIED SUBSTRATES RESULTING THEREFROM

(75) Inventors: Yongxing Qiu, Duluth, GA (US); Lynn Cook Winterton, Alpharetta, GA (US); John Martin Lally, Lilburn, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/911,218

(22) Filed: Jul. 23, 2001

(65) Prior Publication Data

US 2003/0143335 A1 Jul. 31, 2003

Related U.S. Application Data

(60) Provisional application No. 60/228,022, filed on Aug. 24, 2000.

(51) Int. Cl.[7] .......................... A61L 27/00; B05D 1/02; B05D 1/18; B05D 1/36; B05D 1/38
(52) U.S. Cl. ...................... 427/2.24; 427/2.1; 427/2.25; 427/2.28; 427/2.3; 427/164; 427/168; 427/169; 427/407.1; 427/414; 427/415; 427/248.1; 427/421; 427/430.1
(58) Field of Search ............................... 427/169, 414, 427/415, 248.1, 2.1, 2.24, 2.25, 2.28, 2.3, 164, 168, 407, 421, 430.1

(56) References Cited

U.S. PATENT DOCUMENTS

| | | | | |
|---|---|---|---|---|
| 4,168,112 A | * | 9/1979 | Ellis et al. | 351/160 H |
| 4,321,261 A | | 3/1982 | Ellis et al. | 424/180 |
| 4,876,126 A | * | 10/1989 | Takemura et al. | 427/2.1 |
| 4,941,997 A | | 7/1990 | Decher et al. | 252/586 |
| 4,973,429 A | | 11/1990 | Decher et al. | 252/587 |
| 5,068,318 A | | 11/1991 | Decher et al. | 534/573 |
| 5,409,731 A | * | 4/1995 | Nakagawa et al. | 427/164 |
| 5,518,767 A | * | 5/1996 | Rubner et al. | 427/259 |
| 5,529,727 A | | 6/1996 | LaBombard | 264/1.36 |
| 5,536,573 A | | 7/1996 | Rubner et al. | 428/378 |
| 5,807,636 A | * | 9/1998 | Sheu et al. | 428/403 |
| 6,011,082 A | * | 1/2000 | Wang et al. | 523/107 |
| 6,020,175 A | | 2/2000 | Onda et al. | 435/180 |
| 6,050,980 A | * | 4/2000 | Wilson | 427/2.1 |
| 6,087,415 A | * | 7/2000 | Vanderlaan et al. | 424/422 |
| 6,248,127 B1 | * | 6/2001 | Shah et al. | 713/100 |

FOREIGN PATENT DOCUMENTS

| | | |
|---|---|---|
| EP | 0 032 443 A2 | 1/1981 |
| EP | 0 138 385 A2 | 9/1984 |
| EP | 0989418 | 3/2000 |
| GB | 2102070 | 1/1978 |
| JP | 01158412 | 2/1980 |
| JP | 05318118 | 3/1993 |
| WO | WO 95/00618 | 1/1995 |
| WO | WO 95/02251 | 1/1995 |
| WO | WO 95/20407 | 8/1995 |
| WO | WO 96/37241 | 4/1996 |
| WO | WO 96/18498 | 6/1996 |
| WO | WO 96/31792 | 10/1996 |
| WO | WO 98/05269 | 2/1998 |
| WO | WO 99/57581 | 11/1999 |

OTHER PUBLICATIONS

Patterned Polymer Multilayer Fabrication By Controlled Adhesion Of Polyelectrolytes To Plasma–Modified Fluoropolymer Surfaces By Vargo, Calvert, Wynne, Avlyanov, MacDiarmid, & Rubner 1966.
Molecular Self Assembly of Conducting Polymers: A New Layer–By–Layer Thin Film Deposition Process. By Cheung, Fou, Ferrira, & Rubner. MIT.
Blood Capatibility–Surface Characteristic Relationships of a Langmuir–Blodgett Film Composed of an Anionic Amphiphile–Polycation Complex, Uchida M., et al., New Polymers Material, vol. 4, No. 3 pp. 119–211 (1994).
Enhancement of Light Emitting Diodes Based on Self–Assembled Heterosctructures of Poly (P–phenylene vinylene), O. Onitsuka, et al., Journal Applied Physics, 80, (7), Oct. 1, 1996, ppg 4067–4071.
Investigations of New Self–Assembled Multilayer Thin Films Based on Alternately Absorbed Layers of Polyelectrolytes and Functional Dye Molecules, D. Yoo, et al., Material Resource, Soc. Symp. Proc. vol. 413, 1996, Materials Research Society.
New Electro–Active Self–Assembled Multilayer Thin Films Based on Alternately Absorbed Layers of Polyelectrolytes and Functional Dye Molecules, D. Yoo, et al., Elsevier Science, S.A., 1977, ppg 1425–1426.
Layer–By–Layer Modification of Surfaces Through the Use of Self–Assembled Monolayers of Polyions, D. Yoo, et al., ANTEC, 1995 ppg 2568–2570.
Molecular–Level Processing of Conjugated Polymers 1. Layer–by–Layer Manipulation of Conjugated Polyions, M. Ferreira, et al., Macromolecules, vol. 28, No. 21, 1995, ppg 7107–7114.
Molecular–Level Processing of Conjugated Polymers 2. Layer–by–Layer Manipulation of In–Situ Polymerized p–type Doped Conduction Polymers, M. Ferreira, et al., Macromolecules, vol. 28, No. 21, 1995, ppg 7115–7120.
Molecular–Level Processing of Conjugated Polymers 3. Layer–by–Layer Manipulation of Polyaniline via Electrostatic Interactions, J. H. Cheung et al., Macromolecules, 1997, 30, ppg 2712–2716.
International Search Report.

* cited by examiner

Primary Examiner—Jennifer Kolb Michener
(74) Attorney, Agent, or Firm—Jian Zhou; Robert Gorman; R. Scott Meece

(57) ABSTRACT

The present invention generally relates to a method of modifying the surface of substrates such as contact lenses and other biomedical articles by at least partially coating the surfaces of such substrates with a polymeric tie layer having reactive sites. Various other moieties may then be chemically attached to the article surface by reaction of the other moieties with the reactive sites through classical chemical attachment mechanisms.

19 Claims, No Drawings

PROCESS FOR SURFACE MODIFYING SUBSTRATES AND MODIFIED SUBSTRATES RESULTING THEREFROM

This application claims the benefit of provisional application Ser. No. 60/228,022 filed Aug. 24, 2000.

FIELD OF THE INVENTION

The present invention generally relates to a method of modifying the surface of substrates such as contact lenses and other biomedical articles by at least partially coating the surfaces of such substrates with a reactive polymeric tie layer.

BACKGROUND OF THE INVENTION

Many devices used in biomedical applications require that the bulk of the device have one property and the surface of the device have a different property. For example, contact lenses may require relatively high oxygen permeability through the bulk of the lens to maintain good corneal health. However, materials that exhibit exceptionally high oxygen permeability (e.g. polysiloxanes) are typically hydrophobic and, untreated or not surface modified, will adhere to the eye. Thus, a contact lens will generally have a core or bulk material that is highly oxygen permeable and hydrophobic, and a surface that has been treated or coated to increase hydrophilic properties. This hydrophillic surface allows the lens to move relatively freely on the eye without adhering excessive amounts of tear lipid and protein.

A known method for modifying the hydrophilicity of a relatively hydrophobic contact lens material is through the use of a plasma treatment. Plasma treatment techniques are disclosed, for example, PCT Publication Nos. WO 96/31793 to Nicholson et al., WO 99/57581 to Chabrececk et al., and WO 94/06485 to Chatelier et al. In the Chabrececk et al. application, photoinitiator molecules are covalently bound to the surface of the article after the article has been subjected to a plasma treatment which provides the surface with functional groups. A layer of polymerizable macromonomer is then coated onto the modified surface and heat or radiation is applied to graft polymerize the macromonomer to form the hydrophilic surface.

Plasma treatment processes, however, require a significant capital investment in plasma processing equipment. Moreover, plasma treatments take place in a vacuum and, thus, require that the substrate be mostly dry before exposure to the plasma. Thus, substrates, such as contact lenses, that are wet from prior hydration or extraction processes must be dried, thereby further adding to both the capital and production costs. As a result of the conditions necessary for plasma treatment, the incorporation of a plasma treatment process into an automated production process is extremely difficult.

Other methods of permanently altering the surface properties of polymeric biomaterials, such as contact lenses, have been developed. Some of these techniques include Langmuir-Blodgett deposition, controlled spin casting, chemisorptions, and vapor deposition. Examples of Langmuir-Blodgett layer systems are disclosed in U.S. Pat. Nos. 4,941,997; 4,973,429; and 5,068,318. Like plasma treatments, these techniques are not cost-effective methods that may easily be incorporated into automated production processes for making biomedical devices such as contact lenses.

A more recent technique developed for coating substrates is a layer-by-layer ("LbL") polymer absorption process, which is described in "Investigation of New Self-Assembled Multilayer Thin Films Based on Alternately Adsorbed Layers of Polyelectrolytes and Functional Dye Molecules" by Dongsik Yoo, et al. (1996). The process described in this article involves alternatively dipping hydrophilic glass substrates in a polyelectrolyte solution (e.g., polycations such as polyallylamine or polyethyleneimine) and then in an oppositely charged solution to form electrically conducting thin films and light-emitting diodides (LEDs).

Two other similar processes are described in "Molecular-Level Processing of Conjugated Polymers" by Fou & Rubner and Ferreira & Rubner, respectively. These processes involve treating glass substrates that have hydrophilic, hydrophobic, negatively, or positively charged surfaces. The glass surfaces are treated for extended periods in hot acid baths and peroxide/ammonia baths to produce a hydrophilic surface. Hydrophobic surfaces are produced by gas-phase treatment in the presence of 1,1,1,3,3,3-hexamethyldisilazane for 36 hours. Charged surfaces are prepared by covalently anchoring charges onto the surface of the hydrophilic slides. For example, positively charged surfaces are made by further treating the hydrophilic surfaces in methanol, methanol/toluene, and pure toluene rinses, followed by immersion in (N-2 aminoethyl-3-aminopropyl) trimethyloxysilane solution for 12 to 15 hours. This procedure produces glass slides with amine functionalities, which are positively charged at a low pH.

In addition to the above-described techniques, U.S. Pat. Nos. 5,518,767 and 5,536,573 to Rubner et al. describe methods of producing bilayers of p-type doped electrically conductive polycationic polymers and polyanions or water-soluble, non-ionic polymers on glass substrates. These patents describe extensive chemical pre-treatments of glass substrates that are similar to those described in the aforementioned articles.

Various layer-by-layer polyelectrolyte deposition techniques have also been developed by the assignee of the present invention. These layer-by-layer techniques effectively alter the surfaces of various materials, such as contact lenses. One such technique is described in co-pending U.S. Patent Application Ser. No. 60/180,576 filed on Feb. 4, 2000, entitled "Apparatus, Methods, and Compositions for Modifying Surface Characteristics". In particular, a layer-by-layer technique is described that involves consecutively dipping a substrate into oppositely charged polyionic materials until a coating of a desired thickness is formed.

In addition, another technique that results in a layer-by-layer coating while avoiding the time-consuming aspects of sequential dipping, is the single dip process disclosed in co-pending U.S. Patent Application Ser. No. 60/180,463 filed on Feb. 4, 2000, entitled "Single-Dip Process for Achieving a Layer-by-Layer-Like Coating", which applies polyionic material onto the substrate with only a single dip. In this technique, a generally hydrophobic article such as a contact lens is dipped into a single polyionic solution containing at least one polycationic material and at least one polyanionic material. The polycationic material may include a positively charged moiety such as poly(allyl amine hydrochloride) and the polyanionic material may include a negatively charged moiety such as polyacrylic acid. Typically, the polyionic components are employed in non-stoichiometric amounts such that one of the components is present within the solution in a greater amount than another component.

Each of these surface modification techniques are effective for producing a substrate with a surface that is different from the remainder of the substrate. It would be particularly desirable if such modified surfaces were capable of adhering various active agents, such as anti-microbial agents, or other substances, such as photo-initiators, organoselenium, etc. to the substrates. In addition, it would be desirable if such substrate surfaces contained reactive sites for attaching agents through classical chemical attachments processes such as precipitations reactions, hydrogen bonding, electrostatic deposition processes, free radical-initiated polymerization reactions, condensation reactions, and the like.

SUMMARY OF THE INVENTION

Some of the shortcomings of the prior art are overcome with the present invention, which is directed to a method for modifying the surface of substrates, such as contact lenses and other biomedical articles, by at least partially coating the surfaces of such substrates with a reactive polymeric tie layer. The reactive polymeric tie layer, which is generally deposited onto the substrate surface as a polyelectrolytic layer, provides reactive sites for the further attachment of various agents to the substrate. In other words, the polymeric tie layer creates active moieties on the substrate surface through functionalization of the surface by coating with a polyanion and/or polycation. Additional chemistry, such as precipitations reactions, hydrogen bonding, electrostatic deposition processes, free radical-initiated polymerization reactions, condensation reactions, and the like, can then be performed on these active moieties by reacting the moieties with various agents.

Various methods can be utilized to attach the reactive moieties of the polymeric tie layer to the substrate surface. One such method for creating the reactive sites is a layer-by-layer coating application that utilizes successive dips, sprays, or other applications of first a polyanionic layer, and then a polycationic layer. Additional polyelectrolytic tie layers may be applied by this successive application method. Another method applicable to the present invention is a single dip method that utilizes a bicomponent solution containing both a polycationic substance and a polyanionic substance in a single solution.

Among the various polyelectrolytes that can be utilized in such polymeric tie layer coating processes are polyacrylic acid and poly(allyl amine hydrochloride). For example, a polyacrylic acid coating will provide carboxyl functional groups (—COOH) on the surface; and a poly(allyl amine hydrochloride) coating will provide amino functional groups (—NH$_2$) on the surface. These reactive groups may then be further reacted with additional desired molecules or compounds such as various monomers or active agents such as anti-microbials.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The present invention is generally directed to the modification of a substrate surface by utilizing a method of coating the surface with various polyelectrolyte functional groups. The polycationic and/or polyanionic functional groups provide reactive sites to which various other chemical substances may be bounded through traditional or non-traditional chemical reactions or attachment mechanisms.

In accordance with the present invention, a coating process is provided that can be utilized to deposit polyionic materials onto a substrate to form polymeric tie layers having functional groups thereon so that additional active agents can be attached thereto. In one embodiment, for example, a process of the present invention allows the deposition of a bicomponent polyionic solution to a biomaterial substrate, such as a contact lens.

In accordance with the present invention, a polyionic solution is employed to coat the substrate. In general, the polyionic solution contains at least one polycationic material and at least one polyanionic material, although more than one of each polyionic material can be employed. In one embodiment, for example, the polyionic solution is a bicomponent solution containing a polycation and a polyanion.

Typically, a polycationic material of the present invention can include any material known in the art to have a plurality of positively charged groups along a polymer chain, such as poly(allyl amine hydrochloride). Likewise, a polyanionic material of the present invention can typically include any material known in the art to have a plurality of negatively charged groups along a polymer chain, such as polyacrylic acid.

According to one embodiment of the present invention, a polycationic material is combined with a polyanionic material to form a "single-dip" polyionic solution as set forth in U.S. Patent Application Ser. No. 60/180,463 described above, which is incorporated herein in its entirety by reference thereto. In general, the polyionic components are added in non-stoichiometric amounts such that one of the components is present within the solution in a greater amount than another component of opposite charge. In particular, the molar charge ratio, as defined herein, can be from about 3:1 to about 100:1. In certain embodiments, the molar charge ratio is 10:1 (polyanion:polycation).

Layers of polyionic components can be coated onto the substrate. For example, in one embodiment, polyanionic-polycationic-polyanionic alternating repeating layers are assembled when the substrate is dipped into the solution.

Besides containing polyionic components, a polyionic solution of the present invention can also contain various other materials. For example, the polyionic solution can contain antimicrobials, antibacterials, radiation-absorbing materials, cell growth inhibitors, etc.

In other embodiments, the substrate can be dipped in sequentially into separately-charged polyelectrolyte solutions. In these embodiments, a solution of polycationic material may be the first stage dip and a solution of polyanionic material may be the second stage dip (or vice versa). Additional polyionic materials may be utilized in successive stages as described in U.S. Patent Application No. 60/180, 576 set forth above, which is incorporated herein in its entirety by reference thereto.

In general, a surface-modified device of the present invention can be made from various materials. Examples of suitable substrate materials include quartz, ceramics, glasses, silicate minerals, silica gels, metals, metal oxides, carbon materials such as graphite or glassy carbon, natural or synthetic organic polymers, or laminates, composites or blends of such materials, including natural or synthetic organic polymers or modified biopolymers which are well-known. Examples of polymers include polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinyl acetate and polyacrylonitrile); or elastomers (silicones, polybutadiene and polyisoprene).

A particular group of bulk materials from which the inventive substrates may be formed comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

One embodiment of a suitable substrate material of the present invention is a copolymer formed from the following monomeric and macromeric components:

(a) about 5 to about 94 dry weight percent of a macromer having the segment of the formula:

CP-PAO-DU-ALK-PDMS-ALK-DU-PAO-CP where
PDMS is a divalent poly(disubstituted siloxane),
ALK is an alkylene or alkylenoxy group having at least 3 carbon atoms,
DU is a diurethane-containing group,
PAO is a divalent polyoxyalkylene, and
CP is selected from acrylates and methacrylates,
wherein said macromer has a number-average molecular weight of about 2000 to about 10,000;

(b) about 5 to about 60 weight percent methacryloxypropyltris (trimethylsiloxy)silane;

(c) about 1 to about 30 weight percent of an acrylate or methacrylate monomer; and (d) 0 to about 5 weight percent cross-linking agent, with the weight percentages being based upon the dry weight of the polymer components.

Moreover, a particular polysiloxane macromer segment is defined by the formula:

CP-PAO-DU-ALK-PDMS-ALK-DU-PAO-CP where
PDMS is a divalent poly(disubstituted siloxane);
CP is an isocyanatoalkyl acrylate or methacrylate, preferably isocyanatoethyl methacrylate, where the urethane group is bonded to the terminal carbon on the PAO group;

PAO is a divalent polyoxyalkylene (which may be substituted), and is preferably a polyethylene oxide, i.e., $(-CH_2-CH_2-O-)_m CH_2-CH_2-$ where m may range from about 3 to about 44, more preferably about 4 to about 24;

DU is a diurethane (which may be a cyclic structure), where an oxygen of the first urethane linkage is bonded to the PAO group and an oxygen of the second urethane linkage is bonded to the ALK group;

and ALK is an alkylene or alkylenoxy group having at least 3 carbon atoms, such as a branched alkylene group or an alkylenoxy group having 3 to 6 carbon atoms, such as a sec-butyl (i.e., $-CH_2CH_2CH(CH_3)-$) group or an ethoxypropoxy group (e.g., $-O-(CH_2)_2-O-(CH_2)_3-$).

Another embodiment of a suitable substrate material of the present invention is a macromer having the following general formula I:

$$P_1-(Y)_m-(L-X_1)_p-Q-(X_1-L)_p-(Y)_m-P_1$$

where each $P_1$, independently of the others, is a free radical-polymerizable group;

each Y, independently of the others, is $-CONHCOO-$, $-CONHCONH-$, $-OCONHCO-$, $-NHCONHCO-$, $-NHCO-$, $-CONH-$, $-NHCONH-$, $-COO-$, $-OCO-$, $-NHCOO-$ or $-OCONH-$;

m and p, independently of one another, are 0 or 1;
each L, independently of the others, is a divalent radical of an organic compound having up to 20 carbon atoms;
each $X_1$, independently of the others, is $-NHCO-$, $-CONH-$, $-NHCONH-$, $-COO-$, $-OCO-$, $-NHCOO-$ or $-OCONH-$; and
Q is a bivalent polymer fragment consisting of the segments:

(a) $-(E)_k-Z-CF_2-(OCF_2)_x-(OCF_2CF_2)_y-OCF_2-Z-(E)_k-$,

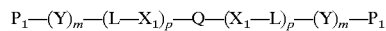

where x+y is a number in the range of about 10 to about 30;
each Z, independently of the others, is a divalent radical having up to about 12 carbon atoms or Z is a bond;
each E, independently of the others, is $-(OCH_2CH_2)_q-$, where q has a value of from 0 to about 2, and where the link $-Z-E-$ represents the sequence $-Z-(OCH_2CH_2)_q-$; and
k is 0 or 1;

(b)

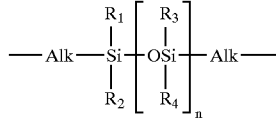

where n is an integer from about 5 to about 100;
Alk is alkylene having up to about 20 carbon atoms;
about 80% to about 100% of the radicals $R_1$, $R_2$, $R_3$ and $R_4$, independently of one another, are alkyl and 0 to about 20% of the radicals $R_1$, $R_2$, $R_3$ and $R_4$, independently of one another, are alkenyl, aryl or cyanolkyl; and (c) $X_2-R-X_2$,
where R is a divalent organic radical having up to 20 carbon atoms; and
each $X_2$, independently of the others, is $-NHCO-$, $-CONH-$, $-NHCONH-$, $-COO-$, $-OCO-$, $-NHCOO-$, or OCONH$-$;

with the provisos that there is typically at least one of each segment (a), (b), and (c) in Q, that each segment (a) or (b) has a segment (c) attached to it, and that each segment (c) has a segment (a) or (b) attached to it.

The number of segments (b) in the polymer fragment may be greater than or equal to the number of segments (a). The ratio between the number of segment (a) and (b) in the polymer fragment Q, for example, may be about 3:4, 2:3, 1:2 or 1:1. The molar ratio between the number of segments (a) and (b) in the polymer fragment Q may be, for example, 2:3, 1:2 or 1:1.

The mean molecular weight of the polymer fragment Q is in the range of about 1,000 to about 20,000, sometimes in the range of about 3000 to about 15,000, and sometimes in the range of about 5,000 to about 12,000.

The total number of segments (a) and (b) in the polymer fragment Q may be in the range of about 2 to about 11, in the range of about 2 to about 9, or in the range of about 2 to about 7. The smallest polymer unit Q may be composed of one perfluoro segment (a), one siloxane segment (b) and one segment (c).

In still another embodiment of the present invention, the substrate material can be formed by polymerizing macromers that contain free hydroxyl groups. Macromers that are built up, for example, from an amino-alkylated polysiloxane derivatized with at least one polyol component that contains an unsaturated polymerizable side chain may be utilized. In one embodiment, polymers can be prepared from the macromers according to the invention by homopolymerization. The macromers mentioned can also be mixed and polymerized with one or more hydrophilic and/or hydrophobic comonomers. A special property of the macromers according to the invention is that they function as the element which controls microphase separation between selected hydrophilic and hydrophobic components in a cross-linked end product. The hydrophilic/hydrophobic microphase separation is in the region of less than about 300 nm. The macromers may be cross-linked at the phase boundaries between, for example, an acrylate comonomer on the one hand and an unsaturated polymerizable side chain of polyols bonded to polysiloxane by covalent bonds, and additionally by reversible physical interactions such as hydrogen bridges/bonds. These are formed, for example, by numerous amide or urethane groups. The continuous siloxane phase that exists in the phase composite has the effect of producing a high permeability to oxygen.

The polymers of this embodiment can be formed by polymerizing a macromer comprising at least one segment having the following general formula (II):

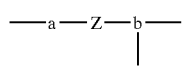

(II)

in which,
(a) is a polysiloxane segment,
(b) is a polyol segment which contains at least 4 carbon atoms,
Z is a segment (c) or a group X1, and
(c) is defined as $X_2$—R—$X_2$, wherein
R is a bivalent radical of an organic compound having up to 20 carbon atoms and
each $X_2$ independently of the other is a bivalent radical which contains at least one carbonyl group, $X_1$ is defined as $X_2$, and
(d) is a radical having the following general formula (III):

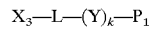

in which, $P_1$ is a group that can be polymerized by free radicals;
Y and $X_3$ independently of one another are a bivalent radical which contains at least one carbonyl group;
k is 0 or 1; and
L is a bond or a divalent radical having up to 20 carbon atoms of an organic compound.

In one embodiment, a polysiloxane segment (a) can be derived from a compound having the following general formula (IV):

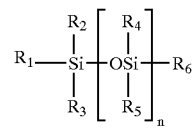

(IV)

in which, n is an integer from 5 to 500;
25%–99.8% of the radicals $R_1$, $R_2$, $R_3$, $R_4$, $R_5$, and $R_6$ independently of one another are alkyl and 0.2%–75% of the radicals $R_1$, $R_2$, $R_3$, $R_4$, $R_5$, and $R_6$ independently of one another are partly fluorinated alkyl, aminoalkyl, alkenyl, aryl, cyanoalkyl, alk-NH-alk-$NH_2$ or alk-$(OCH_2)_m$—$(OCH_2)_p$—$OR_7$,
where $R_7$ is hydrogen or lower alkyl, alk is alkylene, and m and p independently of one another are an integer from 0 to 10, one molecule containing at least one primary amino or hydroxyl group.

The alkylenoxy groups —$(OCH_2CH_2)_m$ and —$(OCH_2)_p$ in the siloxane of the formula (IV) are either distributed randomly in a ligand alk-$(OCH_2CH_2)_m$—$(OCH_2)_p$—$OR_7$ or are distributed as blocks in a chain.

A polysiloxane segment (a) is linked a total of about 1 to about 50 times, and, for example, about 2 to about 30 times, and in particular about 4 to about 10 times, via a group Z with a segment (b) or another segment (a), Z in an a-Z-a sequence typically being a segment (c). The linkage site in a segment (a) with a group Z is an amino or hydroxyl group reduced by one hydrogen.

Another embodiment of a substrate material of the present invention involves the polymerization of a siloxane-containing macromer formed from a poly(dialkylsiloxane) dialkoxyalkanol having the following structure (V):

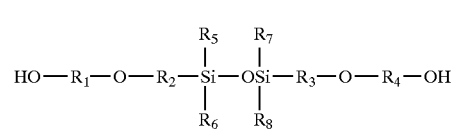

(V)

where n is an integer from about 5 to about 500, preferably about 20 to about 200, more preferably about 20 to about 100;
the radicals $R_1$, $R_2$, $R_3$, and $R_4$, independently of one another, are lower alkylene, for example a $C_1$–$C_6$ alkylene, $C_1$–$C_3$ alkylene, and wherein, in some embodiments, the total number of carbon atoms in $R_1$ and $R_2$ or in $R_3$ and $R_4$ is greater than 4; and
$R_5$, $R_6$, $R_7$, and $R_8$ are, independently of one another, lower alkyl, in some embodiments, a $C_1$–$C_6$ alkyl, and in some embodiments, a $C_1$–$C_3$ alkyl.

The general structure of the macromer discussed above is as follows:

ACRYLATE-LINK-ALK-O-ALK-PDAS-ALK-O-ALK-LINK-ACRYLATE where the ACRYLATE is selected from acrylates and methacrylates; LINK is selected from urethanes and diruretahne linkages, ALK-O-ALK is, as defined above, ($R_1$—O—$R_2$ or $R_3$—O—$R_4$), and PDAS is a poly (dialkylsiloxane).

For example, the macromer described above can be prepared by reacting isophorone diisocyanate, 2-hydroxyethyl (meth)acrylate and a poly(dialkylsiloxane) dialkoxyalkanol in the presence of a catalyst.

A specific group of substrate materials particularly suitable for use in the present invention is the group of materials typically used for the manufacture of biomedical devices such as contact lenses. In particular, contact lenses for extended wear, which are not hydrophilic per se, may have their surfaces made reactive pursuant to the present invention. Such extended wear contact lens materials are known to the skilled artisan and may comprise, for example, polysiloxanes, perfluoroalkyl polyethers, fluorinated poly (meth)acrylates or equivalent fluorinated polymers derived, for example, from other polymerizable carboxylic acids, polyalkyl (meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol.

Specific examples of suitable substrate materials that may be utilized in surface-modified biomedical devices are, for example, Lotrafilcon A, Neofocon, Pasifocon, Telefocon, Silafocon, Fluorsilfocon, Paflufocon, Silafocon, Elastofilcon, or Fluorofocon. In addition, Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene, may be utilized.

Other specific materials that may be used in forming the devices of the present invention include amphiphilic segmented copolymers comprising at least one hydrophobic segment and at least one hydrophilic segment which are linked through a bond or a bridge member. Examples of such materials are silicone hydrogels such as those disclosed in PCT applications WO 96/31792 and WO 97/49740 which are incorporated herein in their entireties by reference thereto. The substrate material to be coated may also be any blood-contacting material typically employed for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™—or Silastic™—type polymer, or a composite made therefrom.

Moreover, the material to be coated may also be an inorganic or metallic base material that, prior to coating, does not contain any appropriate reactive groups. Examples of such base materials include ceramics, quartz, or metals, such as silicon or gold, or various non-reactive polymeric or non-polymeric substrates. Examples of such materials are employed in implantable biomedical applications, where ceramics are common, and in biosensor products, where gold, quartz, or other non-polymeric substrates are common.

The form of the substrate material to be coated may vary within wide limits. Examples are particles, granules, capsules, fibers, tubes, films, and membranes. One particularly useful substrate material will take the form of an article such as ophthalmic molded materials such as intraocular lenses, artificial corneas or contact lenses. In certain embodiments, a substrate material can be made from oxygen-permeable polymeric materials, such as those utilized in the making of certain contact lenses. For example, some examples of suitable contact lens materials, include, but are not limited to, the polymeric materials disclosed in U.S. Pat. No. 5,760,100 to Nicolson et al., which is incorporated herein by reference.

Suitable substances that may be utilized to form the polymeric tie layers of the present invention include various polyelectrolytic materials. One such suitable layer may be formed from a first and second ionic polymer having opposite charges, wherein the "first ionic polymer" indicates the polymer that is first of all applied to the article surface, and the "second ionic polymer" indicates the polymer that is applied to the article surface after it has already been modified with the first ionic polymer. The bulk material may comprise one or more than one such polymeric tie layer. For example, from 1 to 50 tie layers containing the same or different ionic polymers in each case, from 1 to 25 tie layers, from 1 to 20 tie layers, from 1 to 10 tie layers, from 1 to 5 tie layers, or just 1 tie layer may be utilized.

In addition, it may be desirous to have only partial tie layer coverage on the article being treated so that an incomplete tie layer is formed. This may be particularly helpful if only one side of the article needs to be surface modified or if it is desirous to have the two sides of, for example, a contact lens, to have two different coatings—one for the front of the lens and one for the cornea side of the lens.

The polyionic materials that may be employed in the present tie layers include polyanionic and polycationic polymers. Examples of suitable anionic polymers include, for example, a synthetic polymer, a biopolymer or modified biopolymer comprising carboxy, sulfo, sulfato, phosphono or phosphato groups or a mixture thereof, or a salt thereof, for example, a biomedical acceptable salt and especially an ophthalmically acceptable salt thereof when the substrate to be coated is an ophthalmic device.

Specific examples of synthetic anionic polymers include: a linear polyacrylic acid (PAA); a branched polyacrylic acid, for example a Carbophil® or Carbopol® type from Goodrich Corp.; a polymethacrylic acid (PMA); a polyacrylic acid or polymethacrylic acid copolymer, for example, a copolymer of acrylic or methacrylic acid and a further vinylmonomer, for example, acrylamide, N,N-dimethyl acrylamide or N-vinylpyrrolidone; a maleic or fumaric acid copolymer; a poly(styrene-sulfonic acid) (PSS); a polyamido acid, for example, a carboxy-terminated polymer of a diamine and a di- or polycarboxylic acid, for example, carboxy-terminated Starburst™ PAMAM dendrimers (Aldrich); a poly(2-acrylamido-2-methylpropanesulfonic acid) (poly-(AMPS)); or an alkylene polyphosphate, alkylene polyphosphonate, carbohydrate polyphosphate or carbohydrate polyphosphonate, for example, a teichoic acid.

Examples of anionic biopolymers or modified biopolymers are: hyaluronic acid, glycosaminoglycanes, such as heparin or chondroitin sulfate, fucoidan, poly-aspartic acid, poly-glutamic acid, carboxymethyl cellulose, carboxymethyl dextranes, alginates, pectins, gellan, carboxyalkyl chitins, carboxymethyl chitosans, and sulfated polysaccharides.

The anionic polymer may be linear or branched polyacrylic acid or an acrylic acid copolymer, such as a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

Suitable polyanionic material may be any material known in the art to have a plurality of negatively charged groups along a polymer chain. For example, suitable anionic materials can include, but are not limited to:

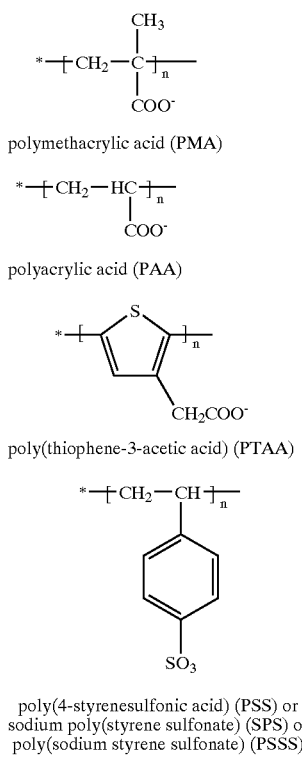

A suitable cationic substance may be any material known in the art to have a plurality of positively charged groups along a polymer chain. A cationic polymer may, for example, be a synthetic polymer, a biopolymer or modified biopolymer comprising primary, secondary or tertiary amino groups or a suitable salt thereof, preferably an ophthalmically acceptable salt thereof when ophthalmic devices are to be coated, for example, a hydrohalogenide, such as a hydrochloride thereof, in the backbone or as substituents.

Various cationic materials can include, but are not limited to:

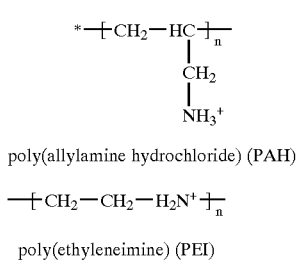

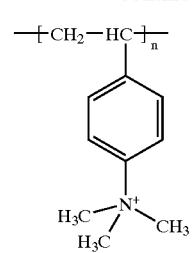

poly(vinylbenzyltriamethylamine) (PVBT)   (c)

polyaniline (PAN or PANI) (p-type doped) or sulphonated polyaniline   (d)

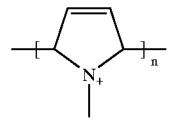

polypyrrole (PPY) (p-typed doped)   (e)

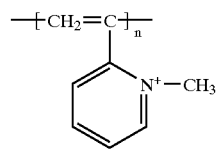

poly(pyridinium acetylene)   (f)

In certain embodiments, either the polyanionic or polycationic material can be made from derivatives of a polyallyl amine having a weight average molecular weight of at least 2000 that, based on the number of amino groups of the polyallyl amine, comprises from approximately 1 to 99% of units having the following formula (1):

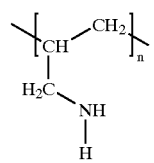

wherein M is a "modifier unit". For instance, in one embodiment, the modifier unit, M, can be R—C=O, where R is $C_2$–$C_6$ alkyl that is substituted by two or more same or different substituents selected from the group consisting of hydroxy, $C_2$–$C_5$ alkanoyloxy, and $C_2$–$C_5$ alkylamino carbonyloxy. Preferably, R is linear $C_3$–$C_6$ alkyl, more preferably linear $C_4$–$C_5$ alkyl, and most preferably n-pentyl that is in each case substituted as defined above.

Suitable substituents of the alkyl radical R are —OH, a radical —O—C(O)—$R_1$, and/or a radical —O—C(O)—NH—$R_1'$, wherein $R_1$ and $R_1'$ are each independently of the other $C_1$–$C_4$ alkyl, preferably methyl, ethyl, iso-, or n-propyl, and more preferably methyl or ethyl. Preferred substituents of the alkyl radical R are hydroxy, acetyloxy, propionyloxy, iso- or n-butanoyloxy, methylaminocarbonyloxy or ethylaminocarbonyloxy, especially hydroxy, acetyloxy, or propionyloxy, and in particular hydroxy.

A particular embodiment of the present invention relates to units of formula (1), wherein R is linear $C_p$-alkyl comprising "p" same or different above-mentioned substituents, and wherein p is 2, 3, 4, 5, or 6, and preferably 4 or 5, and more preferably 5. Alternatively, R may be $C_p$-alkyl comprising "p" hydroxy groups that may be partly or completely acetylated, wherein p is 4 or 5, and preferably 6. Particular radicals R are 1,2,3,4,5-pentahydroxy-n-pentyl or 1,2,3,4,5-pentahydroxy-n-pentyl, wherein the hydroxy groups are partly or completely acetylated.

As stated above, embodiments of a polyionic material of the present invention include derivatives of a polyallyl amine that, based on the number of amino groups of the polyallyl amine, comprise from about 1 to about 99%, in some embodiments from about 10 to about 80%, in some embodiments from about 15 to about 75%, and in other embodiments from about 40 to about 60%, of units of formula (1). In general, polyionic materials of the present invention are also water-soluble.

A particular group of polyallyl amine polymers useful in the present invention comprise at least 1%, in some cases at least 5%, and in other cases at least 10% of units of PAH, and in others at least 20% of units of PAH, based on the number of amino groups of the polyallyl amine. Moreover, one group of polyallyl amine polymers may have a weight average molecular weight of, for example, from 2,000 to 1,000,000, from 3,000 to 500,000, from 5,000 to 150,000, or more particularly from 7,500 to 100,000.

The polyallyl amine polymers described above may be prepared by any manner known in the art. For example, a polyallyl amine having a weight average molecular weight of at least 2,000 that comprises units of PAH may be reacted with a lactone having the following formula (6):

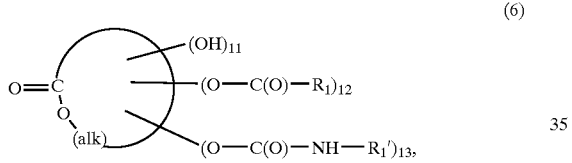

(6)

wherein (alk) is linear or branched $C_2$–$C_6$-alkylene, the sum of (t1-t2-t3) is at least 1, and $R_1$ and $R_1'$ as defined above, to yield a polyallyl amine polymer comprising units of formula (1) and PAH.

The reaction between the polyallyl amine and the lactone may be performed in any manner known in the art, such as, by reacting the polyallyl amine with the lactone in an aqueous medium at a temperature from about 20° C. to about 100° C., and, in some cases, from 30° C. to 60° C. The ratio of units of formula (1) and formula PAH in the final polymer is determined by the stoichiometry of the reactants. The lactones of formula (6) are known or may be prepared according to known methods. Compounds of formula (6), wherein t2 or t3≧1 are, for example, available by reacting the respective hydroxy compound of formula (6) with a compound $R_1$—C(O)X or $R_1'$—NCO under conditions well known in the art. Polyallyl amine starting materials of different molecular weights are commercially available, e.g. in the form of the hydrochloride. Hydrochloride can be converted previously into the free amine, for example, by a treatment with a base, such as sodium or potassium hydroxide solution.

Polyallyl amines comprising additional "modifier units", M, may be prepared by adding to the reaction a mixture of the polyallyl amine and the compound of formula (6), simultaneously or preferably successively. Some examples of compounds that can be added to a polyallyl amine and the compound of formula (6) include, but are not limited to, the following:

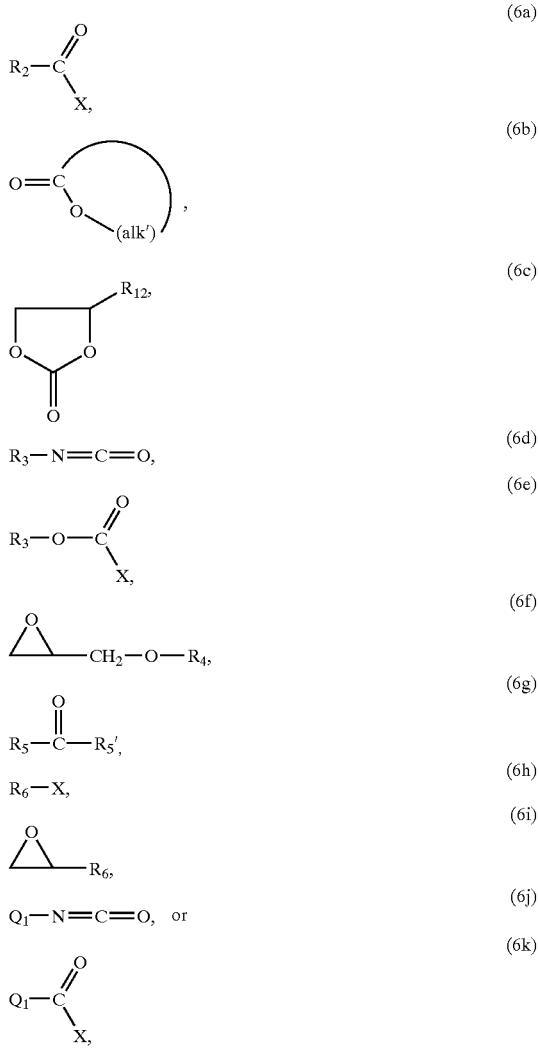

wherein X is halogen, preferably chlorine; (alk') is $C_1$–$C_{12}$-alkylene; $R_{12}$ is hydrogen or $C_1$–$C_2$-alkyl, preferably hydrogen or methyl; and $R_3$, $R_4$, $R_5'$, $R_6$ and $Q_1$ are as defined above. The reaction proceeds, for example, in an aqueous solution at room temperature or at an elevated temperature, such as from 25° C. to about 60° C., and yields various polymers comprising various modifier units.

Because the reaction of the amino groups of the polyallyl amine with the compounds of formulae (6) or (6a)–(6k) proceeds, in general, quantitatively, the structure of the modified polymers is determined mainly by the stoichiometry of the reactants that are employed into the reaction. A particular polyionic material is polyallylamine gluconolactone, as shown below in formula (7):

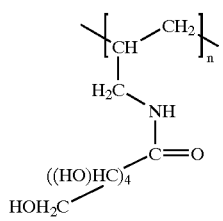

The polyallyl amine may be one in which about 20% to about 80% of the amino groups have been reacted with delta-glucolactone to yield R groups of formula (7).

Further examples of synthetic cationic polymers useful in forming the tie layers of the present invention include:
(i) a polyallylamine (PAH) homo- or copolymer, optionally comprising modifier units as described herein;
(ii) a polyethyleneimine (PEI) as discussed above;
(iii) a polyvinylamine homo- or copolymer, optionally comprising modifier units;
(iv) a poly(vinylbenzyl-tri-$C_1$–$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridin) or poly(vinylpyridinium salt) homo- or copolymer;
(vii) a poly (N,N-diallyl-N,N-di-$C_1$–$C_4$-alkyl-ammoniumhalide);
(viii) a homo- or copolymer of a quaternized di-$C_1$–$C_4$-alkyl-aminoethyl acrylate or methacrylate, for example a poly(2-hydroxy-3-methacyloylpropyltri-$C_1$–$C_2$-alkylammonium salt) homopolymer such as a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed in EP-A-456,467; or
(x) a polyaminoamide (PAMAM), for example a linear PAMAM or a PAMAM dendrimer such as a amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, acrylamide, methacrylamide, N,N-dimethyl acrylamide, N-vinylpyrrolidone and the like.

Examples of cationic biopolymers or modified biopolymers that may be employed in the various tie layers of the present invention include: basic peptides, proteins or glucoproteins, for example, a poly-ϵ-lysine, albumin or collagen, aminoalkylated polysaccharides such as a chitosan or aminodextranes.

Particular cationic polymers for forming the polymer tie layers that are attached to the bulk material of the present invention include a polyallylamine homopolymer; a polyallylamine comprising modifier units of the above formula (1); a polyvinylamine homo- or -copolymer or a polyethyleneimine homopolymer, in particular a polyallylamine or polyethyleneimine homopolymer, or a poly(vinylamine-co-acrylamid) copolymer.

In addition to polyionic materials, a tie layer solution of the present invention can also contain additives. As used herein, an additive can generally include any chemical or material. For example, active agents, such as antimicrobials and/or antibacterials can be added to a tie layer solution of the present invention, particularly when used in biomedical applications. Some antimicrobial polyionic materials include polyquaternary ammonium compounds, such as those described in U.S. Pat. No. 3,931,319 to Green et al. (e.g. POLYQUAD®), which is incorporated herein by reference.

Moreover, others examples of materials that can be added to a tie layer solution of the present invention are polyionic materials useful for ophthalmic lenses, such as materials having radiation absorbing properties. Such materials can include, for example, visibility tinting agents, iris color modifying dyes, and ultraviolet (UV) light tinting dyes.

Still another example of a material that can be added to a tie layer solution of the present invention is a polyionic material that inhibits or induces cell growth. Cell growth inhibitors can be useful in devices that are exposed to human tissue for an extended time with an ultimate intention to remove (e.g. catheters or Intra Ocular Lenses (IOL's), where cell overgrowth is undesirable), while cell growth-inducing polyionic materials can be useful in permanent implant devices (e.g. artificial cornea).

When additives are applied to a tie layer solution of the present invention, such additives have a charge. By having a positive or negative charge, the additive can be substituted for one of the polyionic materials in solution at the same molar charge ratio. For example, polyquaternary ammonium compounds typically have a positive charge. As such, these compounds can be substituted into a solution of the present invention for the polycationic component such that the additive is applied to a substrate material in a manner similar to how a polycationic would be applied.

It should be understood, however, that non-charged additives can also be applied to a substrate material of the present invention. For example, in one embodiment, a polycationic layer can be first applied onto a substrate material. Thereafter, a non-charged additive can be applied and immediately entrapped by a polyanionic material applied thereon. In this embodiment, the polyanionic material can sufficiently entrap the non-charged additive between two layers of polyionic material. After such entrapment, the substrate material can then be coated with other layers of polyionic materials in accordance with the present invention.

As discussed above, a tie layer solution of the present invention can generally be formed from polyionic materials and various other chemicals. In one embodiment, the tie layer solution(s) is a single component system that contains either a cationic or an anionic material that is employed in successive applications. In another embodiment, a tie layer solution of the present invention can be a single-application, bicomponent solution that contains at least one polycationic and polyanionic material. In other embodiments, the tie layer solution can contain more than two components of a polyionic materials, such as 3, 4, 5, or more components.

Regardless of the number of polyionic components present within a single-application, bicomponent tie layer solution of the present invention, it is typically desired that one of the polyionic components of the solution be present in a greater amount than another component such that a non-stoichiometric solution can be formed. For example, when a polyanionic/polycationic bicomponent solution is formed, either one of the polyionic components can be present in an amount greater than the other component. By forming a solution from polyionic materials in such a manner, a substrate material can be suitably coated with the tie layer solution in a single dip.

To control the amount of each polyionic component within a single-application, bicomponent tie layer solution, the "molar charge ratio" can be varied. As used herein, "molar charge ratio" is defined as the ratio of charged molecules in solution on a molar basis. For example, a 10:1 molar charge ratio can be defined as 10 molecules of a polyanion to 1 molecule of a polycation, or 10 molecules of a polycation to 1 molecule of a polyanion. The molar charge ratio can be determined as defined above for any number of components within a solution, as long as at least one polycation and one polyanion are included therein.

As the molar charge ratio is substantially increased, the structure of the tie layer on a particular substrate can become more "open". In some instances, such an opening of the tie layer structure can result in the requirement of more dipping steps to achieve the desired tie layer structure on the substrate material. In this regard, a tie layer solution of the present invention typically has a "molar charge ratio" of from about 3:1 to about 100:1. In one embodiment, the tie layer solution has a molar charge ratio of about 5:1 (polyanion:polycation). In another embodiment, the tie layer solution has a molar charge ratio of about 1:5 (polyanion:polycation). In still another embodiment, a 3:1 or 1:3 molar charge ratio may be utilized.

In a certain embodiment, the tie layer solution has a molar charge ratio of about 10:1 (polyanion:polycation). By employing a tie layer solution having a predominant amount of polyanionic material, a substrate material can be coated in a manner such that the outer layer is a polyanionic material. Substrates having an outer polyanionic material are typically more acidic. It is believed that in some applications, an acidic outer layer can provide a more hydrophilic substrate and allow better wetting, thus allowing hydrophillic coating agents to approach the substrate more intimately. This allows the process to proceed more rapidly. However, it should be understood that an outer layer of polycationic material may also be desirable. In contrast to a polyanionic outer tie layer, a polycationic outer tie layer can be achieved by providing a tie layer solution that contains a predominant amount of polycationic material.

In accordance with the present invention, a tie layer solution, whether a single component solution for sequential dipping or a multi-component for single dipping, the pH level is typically maintained such that the solution remains stable. When the pH of the tie layer solution is improperly varied, a salt can sometimes form through back-titration. Such precipitation can often have an adverse affect on the ability of the tie layer solution to coat the substrate layer as desired. As such, depending on the particular tie layer solution used, the pH of the solution is normally maintained at a value within about ±0.5 of the appropriate pH range for the solution. In certain embodiments, the pH of the tie layer solution is maintained at a pH of ±0.1 of the appropriate pH range for the solution. By maintaining the pH of the solution within a specified range of the appropriate pH for the solution, precipitation can be substantially inhibited.

The appropriate pH range for a tie layer solution can vary depending on the particular polyionic materials chosen. Any suitable method known in the art can be utilized to determine the appropriate pH range for a given solution. One such method is described in "Controlling Bilayer Composition and Surface Wettability of Sequentially Adsorbed Multilayers of Weak Polyelectrolytes" by Dougsik Yoo, Seimel S. Shiratori, and Michael R. Rubner, which is published in MACROMOLECULES® Volume 31, Number 13, pages 4309–4318 (1998). For example, in a particular embodiment for the multi-component tie layer solutions, a 10:1 (polyanion:polycation) ratio of polyacrylic acid and polyallylamine hydrochloride is utilized. For this particular bicomponent tie layer solution, the appropriate pH range was determined to be about 2.5.

The formation and application of the tie layers onto the substrate surface may be accomplished according to various processes. For example, the substrate material may be immersed in a solution containing both an anionic polymer(s) and a cationic polymer(s), or one or more layers each of the anionic polymer(s) and cationic polymer(s) are successively deposited on the substrate material surface, for example, by dipping, spraying, printing, spreading, pouring, rolling, spin coating or vacuum vapor deposition, or spraying. Following the deposition of one ionic polymer, the coated substrate material may be rinsed or dried before the deposition of the next ionic polymer having opposite charges.

One particular dip method involves the steps of (i) applying a tie layer of a first ionic polymer, for example of a cationic or an anionic polymer, to the bulk substrate material by immersing the bulk material in a solution of the first ionic polymer; (ii) optionally, rinsing the bulk material by immersing it in a rinsing solution; (iii) optionally, drying said bulk material; and (iv) applying a tie layer of a second ionic polymer having charges opposite of the charges of the first ionic polymer, for example an anionic or a cationic polymer, to the bulk material by immersing the bulk material in a solution of the second ionic polymer. This particular process is more fully described in U.S. Patent Application Ser. No. 60/180,576, which has been incorporated herein by reference.

A further dip method involves immersing the bulk material in a multi-component solution comprising both the anionic and cationic polymer, as described in U.S. Patent Application Ser. No. 60/180,463, which has been incorporated herein by reference.

Whether a single component solution for sequential dipping or a multi-component for single dipping of the present invention, the dip solutions of the present invention generally comprise the respective polymer diluted in one or more different solvents. Suitable solvents are, for example, water or an aqueous solution comprising a water-miscible organic solvent, for example a $C_1$–$C_4$-alkanol such as methanol or ethanol; the preferred solvent is pure water. The aqueous solutions of the cationic or anionic polymer advantageously each have a slightly acidic pH value, for example a pH from about 2 to about 5 and preferably from about 2.5 to about 4.5. The concentration of the dip solutions may vary within wide limits depending, for example, on the particular ionic polymer involved or the desired thickness. However, it may generally be preferred to formulate relatively dilute solutions of the ionic polymers. A particular anionic or cationic polymer concentration is from about 0.0001 to about 0.25 weight percent, from about 0.0005 to about 0.15 weight percent, from about 0.001 to about 0.25 weight percent, from about 0.005 to about 0.10 weight percent, from about 0.01 to about 0.05 weight percent and, in particular, from 0.001 to 0.1 percent by weight, relative to the total weight of the solution.

A suitable rinsing solution may be an aqueous solution. The aqueous solution may have a pH of about 2 to about 7, from about 2 to about 5, or from about 2.5 to about 4.5.

Partial drying or removal of excess rinsing solution from the surface between solution applications may be accomplished by a number of means known in the art. While the bulk material may be partially dried by merely allowing the coated material to remain in an air atmosphere for a certain period of time, the drying time may be accelerated by application of a mild stream of air to the surface. The flow rate may be adjusted as a function of the strength of the material being dried and the mechanical fixturing of the material.

The thickness of the tie layer may be adjusted by addition of one or more salts, such as sodium chloride, to the ionic polymer solution. A particular salt concentration that may be employed is about 0.1 to about 2.0 weight percent. As the salt concentration is increased, the polyelectrolyte takes on a more globular conformation. However, if the concentration is raised too high, the polyelectrolyte will not deposit well, if at all, on the substrate surface.

The polymeric tie layer formation process may be repeated a plurality of times, for example from 1 to about 50 times, from 1 to about 24 times, from 1 to about 14 times, or only one time.

The immersion time for each of the coating and optional rinsing steps may vary depending on a number of factors. In general, a rinsing time of from about 30 seconds to about 30 minutes, from about 1 to about 20 minutes, from about 1 to about 10 minutes or from about 1 to about 6 minutes may be employed. The immersion in the polymer solutions may take place at various temperatures, such as at room temperature or at a lower temperature.

Instead of coating the substrate material by means of a dip technique, the substrate may be coated using spray coating techniques. The above given conditions and features concerning solvents, concentrations, presence of salts, pH, temperature, number and sequence of coating steps, and rinsing or drying steps apply accordingly. Spray coating technique in this context comprises any known process in the art including, for example, conventional techniques of applying a fluid, or techniques using ultrasonic energy, or electrostatic spray coating techniques. In addition, a mixture of dip and spray techniques may also be employed.

In this regard, an embodiment of the single-application, bicomponent tie layer solution of the present invention can be prepared as follows. However, it should be understood that the following description is for exemplary purposes only and that a tie layer solution of the present invention can be prepared by other suitable methods.

A bicomponent tie layer solution can be prepared by first dissolving a single component polyanionic material in water or other solvent at a designated concentration. For example, in one embodiment, a solution of polyacrylic acid having a molecular weight of about 90,000 is prepared by dissolving a suitable amount of the material in water to form a 0.001M PAA solution. Once dissolved, the pH of the polyanionic solution can be properly adjusted by adding a basic or acid material. In the embodiment above, for example, a suitable amount of 1N hydrochloric acid (HCl) can be added to adjust the pH to 2.5.

After preparing the polyanionic solution, the polycationic solution can be similarly formed. For example, in one embodiment, poly(allylamine hydrochloride) having a molecular weight of about 50,000 to about 65,000 can be dissolved in water to form a 0.001M solution. Thereafter, the pH can be similarly adjusted to 2.5 by adding a suitable amount of hydrochloric acid.

The formed solutions can then be mixed to form a single-dip tie layer solution of the present invention. In one embodiment, for example, the solutions above can be mixed slowly to form the tie layer solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

Once a tie layer solution is formed in accordance with the present invention, it can then be applied to a substrate material by any of the methods described above.

In some embodiments of the present invention, the particular substrate material utilized can also be "pre-conditioned" or "oriented" before being dipped into a tie layer solution. Although not required, pre-conditioning the substrate material in accordance with the present invention can enhance the growth of polyionic layers in the "single dip" type process. In particular, pre-conditioning a substrate material typically involves increasing the roughness of the substrate surface.

In this regard, the roughness of the substrate surface can be altered in a variety of ways. Generally, an "underlayer" or "primer layer" of tie layer solution can be initially applied to the substrate material to accomplish the desired surface alteration. For example, in one embodiment, one or more standard layer-by-layer dip coatings can be employed as an underlayer for the ultimate dip coating of the present invention. The "underlayer" can be applied by any method known in the art, such as by spray-coating, dipping, etc. Examples of such methods are disclosed in detail in co-pending U.S. application Ser. No. 09/199,609. In some embodiments, the underlayer can be made from a polyionic material, such as poly(ethyleneimine). After applying this primer coating or underlayer, in one embodiment, the substrate can then be dipped into the ultimate coating solution. For instance, in one embodiment, the ultimate coating solution can contain poly(allylamine hydrochloride) and polyacrylic acid. In still another embodiment, the tie layer solution can contain poly(allylamine hydrochloride) and sodium poly(styrene sulfonate).

Moreover, in another embodiment, the substrate material can be allowed to swell in a solvent solution containing a solvent and at least one polyionic component(s). In general, any solvent that can allow the components within the tie layer solution to remain stable in water is suitable for use in the present invention. Examples of suitable alcohols can include, but are not limited to, isopropyl alcohol, hexanol, ethanol, etc. In certain embodiments, the substrate material is first allowed to swell in an alcohol solution containing about 20% isopropyl alcohol and about 80% water. In some embodiments, the alcohol solution used to swell the substrate can also be used as the solvent in the ultimate single-dip polyionic tie layer solution.

After swelling, the substrate material can then be removed from the solvent solution and allowed to "shrink". This "shrinking" step causes the substrate material to entrap part or all of the initial layer of the polycation or polyanion present within the solvent solution. The swelling/entrapment process described in this embodiment can enhance the ability of the tie layer solution to coat the substrate material.

However, it may often be desired to apply a tie layer having a substantial thickness that cannot be sufficiently applied with a single dip. For example, in one embodiment of the present invention, a 500 angstrom tie layer (as measured by atomic force microscopy ("AFM")) is applied to a substrate material in two dipping steps. In particular, a 10:1 polyanion to polycation dip is first applied to the substrate material. Thereafter, a 1:10 polyanion to polycation is employed as a second tie layer layer. In some embodiments, more than two dips, such as 3 to 5 dips in multi-component solutions of the present invention can be utilized. For example, when coating a contact lens material according to the present invention, three dips may be utilized.

The molecular weight of the anionic and cationic polymers used to prepare the tie layers may vary within wide limits depending on the desired characteristics such as adhesion on the bulk material, coating thickness and the like. Generally, as the molecular weight of the polyionic materials increases, the tie layer thickness increases. However, if the increase in molecular weight increase is too substantial, the difficulty in handling may also increase. In general, a weight average molecular weight of from about 5000 to about 5,000,000, from about 10,000 to about 1,000,000, from about 15,000 to about 500,000, from about 20,000 to about 200,000, from about 10,000 to about 150,000, from about 25,000 to about 100,000, from about 75,000 to about 100,000, and from about 40,000 to about 150,000, has proven as valuable both for the anionic and cationic polymer forming the tie layer.

According to the above-mentioned methods, substrate materials are obtained that comprise one or more tie layers of polyelectrolytes adsorbed onto and/or heteropolarly bound on the surface. Due to this modification, the surface is provided with functional groups such as, for example, carboxy, sulfone, sulfato, phosphono or phosphato groups or primary, secondary or tertiary amine groups. It is these functional groups that may be further reacted with various agents to form the surface-modified substrates of the present invention.

Polymerization initiators are examples of the various active agents that may be bound to the functional groups in the present invention. Typically, polymerization initiators are capable of initiating a radical polymerization of ethylenically unsaturated compounds. The radical polymerization may be induced thermally or by irradiation. In this regard, PCT Publication No. WO 99/57581 is incorporated herein in its entirety. In particular, various surface initiator moieties for radical polymerization and the various hydrophilic macromonomers suitable for polymerization are disclosed in that application and are applicable to the present invention for attachment to the electrolytic polymeric tie layers.

Generally, suitable thermal polymerization initiators are known to the skilled artisan and comprise, for example, peroxides, hydroperoxides, azo-bis(alkyl- or cycloalkylnitriles), persulfates, percarbonates or mixtures thereof. An example of a functionalized thermal initiator is 4,4'-azo-bis(4-cyanovaleric acid) or derivatives thereof.

Initiators for radiation-induced polymerization are generally functional photoinitiators having a photoinitiator part and a functional group that is coreactive with functional groups of the tie layers, particularly with amino or carboxy groups. The photoinitiator part may belong to different types, for example to the thioxanthone type and, preferably, to the benzoin type. Suitable functional groups that are coreactive with the tie layer(s) attached to the surface of the bulk material are for example a carboxy, hydroxy, epoxy or particularly an isocyanato group.

Among the various polymerization initiators for use in the present invention are the photoinitiators of formulae (I) and (Ia) as disclosed in U.S. Pat. No. 5,527,925, those of the formula (I) as disclosed in PCT application WO 96/20919, or those of formulae II and III including formulae IIa–IIy and IIIg as disclosed in EP-A-0281941, particularly formulae IIb, IIi, IIm, IIn, IIp, IIr, IIs, IIx and IIIg therein. These three documents are incorporated herein by reference thereto.

When polymerization photoinitiators are employed with the present invention, the photoinitiators are attached to the reactive polymeric tie layer's functional groups by covalent bonding. Generally, the covalent bonding will occur via reaction between an amino or a carboxy group of the polymeric tie layer and an isocyanato group of the photoinitiator. Such a reaction may take place at various temperatures, for example from 0° to 100° C. Typically, such a reaction will occur in the presence of a catalyst and any excess compounds may be removed after the reaction with, for example, various solvents.

Alternatively in other embodiments of the present invention, the covalent bonding may take place between the modified surface of the substrate and the photoinitiator through a reaction of a carboxy or isocyanato group at a reactive site of the polymeric tie layer and a hydroxy, amino or alkylamino group of the photoinitiator. Regardless of the particular groups participating in the covalent bonding, such reactions are well-known by those of ordinary skill in the art and may be carried out at the conditions typically employed for effecting such reactions.

A hydrophilic monomer useful to provide the hydrophilic surface coating on the initiator-modified substrate material surface is typically a monomer that yields as homopolymer a polymer that is water-soluble or can absorb at least 10% by weight of water. Examples of various hydrophilic monomers are hydroxy-substituted $C_2$–$C_4$-alkyl acrylates and methacrylates, acrylamide, methacrylamide, N,N-di-$C_1$–$C_4$-alkyl acrylamides and methacrylamides, ethoxylated acrylates and methacrylates, hydroxy-substituted $C_2$–$C_4$-alkyl acrylamides and methacrylamides, hydroxy-substituted $C_1$–$C_4$-alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- or 4-vinylpyridine, acrylic acid, methacrylic acid, amino- (the term "amino" also including quaternary ammonium), mono-$C_1$–$C_4$-alkylamino- or di-$C_1$–$C_4$-alkylamino-$C_1$–$C_4$-alkyl acrylates and methacrylates, allylalcohol and the like. Hydroxy-substituted or N,N-di-$C_1$–$C_2$-alkylamino-substituted $C_2$–$C_4$ alkyl(meth)acrylates, five- to seven-membered N-vinyl lactams, N,N-di-$C_1$–$C_4$ alkyl(meth)acrylamides and vinylically unsaturated carboxylic acids having a total of from 3 to 5 carbon atoms, for example, may be specifically utilized.

Examples of various hydrophilic vinylic monomers that may be employed as the agent attached to the polymeric tie layer on the modified reactive substrate surface include hydroxyethyl methacrylate, hydroxyethyl acrylate, acrylamide, methacrylamide, N,N-dimethylacrylamide, allyl alcohol, N-vinylpyrrolidone, acrylic acid, methacrylic acid and N,N-dimethylaminoethyl methacrylate.

A hydrophilic surface may be created on the substrate in accordance with the present invention by using any suitable macromonomer such as, for example, a macromonomer having the formula

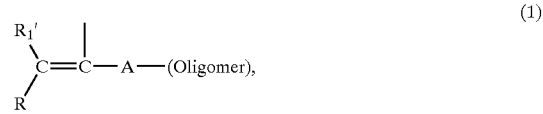
(1)

wherein $R_1$ is hydrogen, $C_1$–$C_6$-alkyl or a radical —COOR';
R, R' and $R_1'$ are each independently of the other hydrogen or $C_1$–$C_6$-alkyl;
A is a direct bond or is a radical of formula

| | |
|---|---|
| —C(O)—$(A_1)_n$—X— | (2a) or |
| —$(A_2)_m$—NH—C(O)—X— | (2b); or |
| —$(A_2)_m$—X—C(O)— | (2c); or |
| —C(O)—NH—C(O)—X— | (2d); or |
| —C(O)—$X_1$—(alk*)—X—C(O)— | (2e); or |

A and $R_1$, together with the adjacent double bond, are a radical of formula

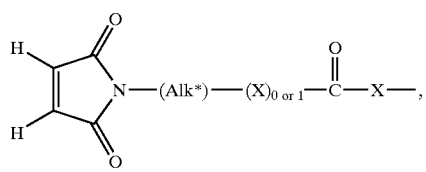
(2f)

$A_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{11}$—NH—C(O)—, wherein $R_{11}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cyclo-alkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cyclo-alkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

wherein (alk) is $C_2$–$C_{12}$-alkylene,

Q is a monovalent group that is suitable to act as a polymerization chain-reaction terminator, p and q are each independently of another an integer from 0 to 250, wherein the total of (p+q) is an integer from 2 to 250, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

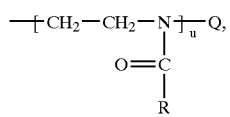
(3b)

wherein $R_{28}$ is hydrogen or unsubstituted or hydroxy-substituted $C_1$–$C_{12}$-alkyl, u is an integer from 2 to 250 and Q' is a radical of a polymerization initiator; or (iii) the radical of formula

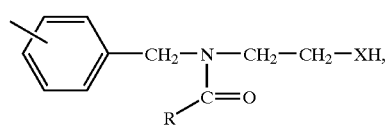
(3b')

wherein $R_{28}$, X and u are as defined above, or (iv) the radical of an oligomer of formula

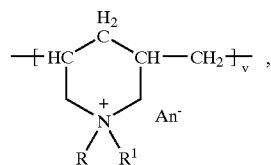
(3c)

wherein $R_2$ and $R_2'$ are each independently $C_1$–$C_4$-alkyl, An⁻ is an anion, v is an integer from 2 to 250, and Q" is a monovalent group that is suitable to act as a polymerization chain-reaction terminator; or (v) the radical of an oligopeptide of formula

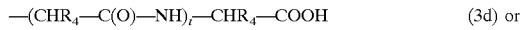
—(CHR$_4$—C(O)—NH)$_t$—CHR$_4$—COOH (3d) or

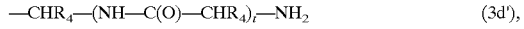
—CHR$_4$—(NH—C(O)—CHR$_4$)$_t$—NH$_2$ (3d'), wherein $R_4$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula

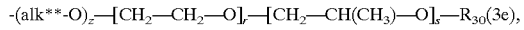
-(alk-O)$_z$—[CH$_2$—CH$_2$—O]$_r$—[CH$_2$—CH(CH$_3$)—O]$_s$—R$_{30}$(3e), wherein $R_{30}$ is hydrogen or $C_1$–$C_{24}$-alkyl, (alk) is $C_2$–$C_4$-alkylene, z is 0 or 1, r and s are each independently an integer from 0 to 250 and the total of (r+s) is from 2 to 250; or (vii) the radical of an oligosaccharide;

subject to the provisos that

A is not a direct bond if (oligomer) is a radical of formula (3a);

A is a direct bond if (oligomer) is a radical of formula (3b');

A is not a radical of formula (2c) or (2e) if (oligomer) is a radical of formula (3b), (3c), (3d), (3e) or is the radical of an oligosaccharide; and A is a radical of formula (2c) or (2e) if (oligomer) is a radical of formula (3d').

The following preferences apply to the variables contained in the definition of the macromonomer of formula (1):

R' is preferably hydrogen or $C_1$–$C_4$-alkyl, more preferably hydrogen or $C_1$–$C_2$-alkyl and particularly preferably hydrogen.

$R_1$ is preferably hydrogen, methyl or carboxyl, and particularly preferably hydrogen.

R is preferably hydrogen or methyl.

X is preferably a bivalent group —O— or —NH—. X is particularly preferably the group —NH— if (oligomer) is a radical of formula (3a); (3c) or (3d), and is particularly preferably the group —O— if (oligomer) is a radical of formula (3b). X' is preferably —O— or —NH— and more preferably —NH—. $X_1$ is preferably —O— or —NH—.

$R_{11}$ as alkylene is preferably a linear or branched $C_3$–$C_{14}$ alkylene radical, more preferably a linear or branched $C_4$–$C_{12}$ alkylene radical and most preferably a linear or branched $C_6$–$C_{10}$alkylene radical.

When $R_{11}$ is arylene, it is, for example, naphthylene or especially phenylene, each of which may be substituted, for example, by $C_1$–$C_4$-alkyl or by $C_1$–$C_4$-alkoxy. Preferably, $R_{11}$ as arylene is 1,3- or 1,4-phenylene that is unsubstituted or substituted by $C_1$–$C_4$-alkyl or by $C_1$–$C_4$-alkoxy in the ortho-position to at least one linkage site. Examples of substituted arylene are 1-methyl-2,4-phenylene, 1,5-dimethyl-2,4-phenylene, 1-methoxy-2,4-phenylene and 1-methyl-2,7-naphthylene.

$R_{11}$ as aralkylene is preferably naphthylalkylene and most preferably phenylalkylene. The alkylene group in aralkylene contains preferably from 1 to 12, more preferably from 1 to 6 and most preferably from 1 to 4 carbon atoms. Most preferably, the alkylene group in aralkylene is methylene or ethylene.

When $R_{11}$ is cycloalkylene, it is preferably $C_5$–$C_6$cycloalkylene and most preferably cyclohexylene that is unsubstituted or substituted by methyl.

When $R_{11}$ is cycloalkylene-alkylene, it is preferably cyclopentylene-$C_1$–$C_4$-alkylene and especially cyclohexylene-$C_1$–$C_4$-alkylene, each unsubstituted or mono- or poly-substituted by $C_1$–$C_4$-alkyl, especially methyl. More preferably, the group cycloalkylene-alkylene is cyclohexylene-ethylene and, most preferably, cyclohexylene-methylene, each unsubstituted or substituted in the cyclohexylene radical by from 1 to 3 methyl groups.

When $R_{11}$ is alkylene-cycloalkylene-alkylene, it is preferably $C_1$–$C_4$-alkylene-cyclopentylene-$C_1$–$C_4$-alkylene and especially $C_1$–$C_4$-alkylene-cyclohexylene-$C_1$–$C_4$-alkylene, each unsubstituted or mono- or poly-substituted by $C_1$–$C_4$-alkyl, especially methyl. More preferably, the group alkylene-cycloalkylene-alkylene is ethylene-cyclohexylene-ethylene and, most preferably, is methylene-cyclohexylene-methylene, each unsubstituted or substituted in the cyclohexylene radical by from 1 to 3 methyl groups.

$R_{11}$ as $C_3$–$C_8$-cycloalkylene-$C_1$–$C_2$-alkylene-$C_3$–$C_8$-cycloalkylene or $C_6$–$C_{10}$-arylene-$C_1$–$C_2$-alkylene-$C_6$–$C_{10}$-arylene is preferably $C_5$–$C_6$-cycloalkylene-methylene-$C_5$–$C_6$-cycloalkylene or phenylene-methylene-phenylene, each of which may be unsubstituted or substituted in the cycloalkyl or phenyl ring by one or more methyl groups.

The radical $R_{11}$ has a symmetrical or, preferably, an asymmetrical structure. A preferred group of radicals $R_{11}$ comprises those, wherein $R_{11}$ is linear or branched $C_6$–$C_{10}$alkylene; cyclohexylene-methylene or cyclohexylene-methylene-cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{11}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl isocyanate), 1,6-diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene-NH—C(O)— and particularly —O—$(CH_2)_{2-4}$—, —O—$CH_2$—CH(OH)—$CH_2$— or a radical —O—$(CH_2)_{2-4}$—NH—C(O)—. A particularly preferred meaning of $A_1$ is the radical —O—$(CH_2)_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene.

n is an integer of 0 or preferably 1. m is preferably an integer of 1.

$R_1$' is preferably hydrogen or methyl and particularly preferably hydrogen.

In case that (oligomer) is a radical of formula (3a), (3b), (3c), (3d), (3e) or is the radical of an oligosaccharide. A preferably denotes a radical of formula (2a) or (2b) and particularly preferably a radical of formula (2a), wherein the above given meanings and preferences apply for the variables contained therein.

A particular group of hydrophilic macromonomers that may be attached to the polymeric tie layers of the present invention comprise compounds of the above formula (1), wherein R is hydrogen or methyl, $R_1$ is hydrogen, methyl or carboxyl, $R_1$' is hydrogen, A is a radical of the formula (2a) or (2b) and (oligomer) is a radical of formula (3a), (3b), (3c), (3d), (3e) or is the radical of an oligosaccharide. Another group of potential hydrophilic macromonomers comprises compounds of the above formula (1), wherein R is hydrogen or methyl, $R_1$ and $R_1$' are each hydrogen, A is a radical of the formula (2a) and (oligomer) is a radical of formula (3a). A further group of macromonomers comprises compounds of formula (1), wherein A is a radical of formula (2e) above and (oligomer) is a radical of formula (3a).

(alk) and (alk*) are each independently preferably $C_2$–$C_8$-alkylene, more preferably $C_2$–$C_6$-alkylene, even more preferably $C_2$–$C_4$-alkylene and particularly preferably 1,2-ethylene. The alkylene radicals (alk) and (alk*) may be branched or preferably linear alkylene radicals.

Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50. In a further preferred embodiment p is from 4 to 99, q is from 1 to 96 and the total of (p+q) is from 5 to 100.

Suitable hydrophilic substituents of the radicals B or B' may be nonionic, anionic, cationic or zwitterionic substituents. Accordingly, the telomer chain of formula (3a) that contains monomer units B and/or B' may be a charged chain containing anionic, cationic and/or zwitterionic groups or may be an uncharged chain. In addition, the telomer chain may comprise a copolymeric mixture of uncharged and charged units. The distribution of the charges within the telomer, if present, may be random or blockwise.

In one embodiment of the invention, the telomer radical of formula (3a) is composed solely of non-ionic monomer units B and/or B'. In another preferred embodiment of the invention, the telomer radical of formula (3a) is composed solely of ionic monomer units B and/or B', for example solely of cationic monomer units or solely of anionic monomer units. Still another embodiment of the invention is directed to telomer radicals of formula (3a) comprising nonionic units B and ionic units B'.

Suitable non-ionic substituents of B or B' include for example a radical $C_1$–$C_6$-alkyl which is substituted by one or more same or different substituents selected from the group consisting of —OH, $C_1$–$C_4$-alkoxy and —$NR_9R_9$', wherein $R_9$ and $R_9$' are each independently of another hydrogen or unsubstituted or hydroxy-substituted $C_1$–$C_6$-alkyl or phenyl; phenyl which is substituted by hydroxy, $C_1$–$C_4$-alkoxy or —$NR_9R_9$', wherein $R_9$ and $R_9$' are as defined above; a radical —COOY, wherein Y is $C_1$–$C_{24}$-alkyl which is unsubstituted or substituted, for example, by hydroxy, $C_1$–$C_4$-alkoxy, —O—$Si(CH_3)_3$, —$NR_9R_9$' wherein $R_9$ and $R_9$' are as defined above, a radical —O—$(CH_2CH_2O)_{1-24}$—E wherein E is hydrogen or $C_1$–$C_6$-alkyl, or a radical.

—NH—C(O)—O—G, wherein —O—G is the radical of a saccharide with 1 to 8 sugar units or is a radical —O—

($CH_2CH_2O)_{1-24}$—E, wherein E is as defined above, or Y is $C_5$–$C_8$-cycloalkyl which is unsubstituted or substituted by $C_1$–$C_4$-alkyl or $C_1$–$C_4$-alkoxy, or is unsubstituted or $C_1$–$C_4$-alkyl- or $C_1$–$C_4$-alkoxy-substituted phenyl or $C_7$–$C_{12}$-aralkyl; —$CONY_1Y_2$ wherein $Y_1$ and $Y_2$ are each independently hydrogen, $C_1$–$C_{12}$-alkyl, which is unsubstituted or substituted for example by hydroxy, $C_1$–$C_4$-alkoxy or a radical —O—($CH_2CH_2O)_{1-24}$—E wherein E is as defined above, or $Y_1$ and $Y_2$ together with the adjacent N-atom form a five- or six-membered heterocyclic ring having no additional heteroatom or one additional oxygen or nitrogen atom; a radical —$OY_3$, wherein $Y_3$ is hydrogen; or $C_1$–$C_{12}$-alkyl which is unsubstituted or substituted by —$NR_9R_9'$; or is a radical —C(O)—$C_1$–$C_4$-alkyl; and wherein $R_9$ and $R_9'$ are as defined above; or a five- to seven-membered heterocyclic radical having at least one N-atom and being bound in each case via said nitrogen atom.

Suitable anionic substituents of B or B' include for example $C_1$–$C_6$-alkyl which is substituted by —$SO_3H$, —$OSO_3H$, —$OPO_3H_2$ and —COOH; phenyl which is substituted by one or more same or different substituents selected from the group consisting of —$SO_3H$, —COOH, —OH and —$CH_2$—$SO_3H$; —COOH; a radical —$COOY_4$, wherein $Y_4$ is $C_1$–$C_{24}$-alkyl which is substituted for example by —COOH, —$SO_3H$, —$OSO_3H$, —$OPO_3H_2$ or by a radical —NH—C(O)—O—G' wherein G' is the radical of an anionic carbohydrate; a radical —$CONY_5Y_6$ wherein $Y_5$ is $C_1$–$C_{24}$-alkyl which is substituted by —COOH, —$SO_3H$, —$OSO_3H$, or —$OPO_3H_2$ and $Y_6$ independently has the meaning of $Y_5$ or is hydrogen or $C_1$–$C_{12}$-alkyl; or —$SO_3H$; or a salt thereof, for example a sodium, potassium, ammonium or the like salt thereof.

Suitable cationic substituents of B or B' include $C_1$–$C_{12}$-alkyl which is substituted by a radical —$NR_9R_9'R_9''^+An^-$, wherein $R_9$, $R_9'$ and $R_9''$ are each independently of another hydrogen or unsubstituted or hydroxy-substituted $C_1$–$C_6$-alkyl or phenyl, and $An^-$ is an anion; or a radical —C(O)$OY_7$, wherein $Y_7$ is $C_1$–$C_{24}$-alkyl which is substituted by —$NR_9R_9'R_9''^+An^-$ and is further unsubstituted or substituted for example by hydroxy, wherein $R_9$, $R_9'$, $R_9''$ and $An^-$ are as defined above.

Suitable zwitterionic substituents of B or B' include a radical —$R_3$—Zw, wherein $R_3$ is a direct bond or a functional group, for example a carbonyl, carbonate, amide, ester, dicarboanhydride, dicarboimide, urea or urethane group; and Zw is an aliphatic moiety comprising one anionic and one cationic group each.

The following preferences apply to the hydrophilic substituents of B and B':

(i) Non-ionic Substituents:

Preferred alkyl substituents of B or B' are $C_1$–$C_4$-alkyl, in particular $C_1$–$C_2$-alkyl, which is substituted by one or more substituents selected from the group consisting of —OH and —$NR_9R_9'$, wherein $R_9$ and $R_9'$ are each independently of another hydrogen or $C_1$–$C_4$-alkyl, preferably hydrogen, methyl or ethyl and particularly preferably hydrogen or methyl, for example —$CH_2$—$NH_2$, —$CH_2$—$N(CH_3)_2$.

Preferred phenyl substituents of B or B' are phenyl which is substituted by —$NH_2$ or $N(C_1$–$C_2$-alkyl$)_2$, for example o-, m- or p-aminophenyl.

In case that the hydrophilic substituent of B or B' is a radical —COOY, Y as optionally substituted alkyl is preferably $C_1$–$C_{12}$-alkyl, more preferably $C_1$–$C_6$-alkyl, even more preferably $C_1$–$C_4$-alkyl and particularly preferably $C_1$–$C_2$-alkyl, each of which being unsubstituted or substituted as mentioned above. In case that the alkyl radical Y is substituted by —$NR_9R_9'$, the above-given meanings and preferences apply for $R_9$ and $R_9'$. Examples of suitable saccharide substituents —O—G of the alkyl radical Y that is substituted by —NH—C(O)—O—G are the radical of a mono- or disaccharide, for example glucose, acetyl glucose, methyl glucose, glucosamine, N-acetyl glucosamine, glucono lactone, mannose, galactose, galactosamine, N-acetyl galactosamine, fructose, maltose, lactose, fucose, saccharose or trehalose, the radical of an anhydrosaccharide such as levoglucosan, the radical of a glucosid such as octylglucosid, the radical of a sugar alcohol such as sorbitol, the radical of a sugar acid derivative such as lactobionic acid amide, or the radical of an oligosaccharide with a maximum of 8 sugar units, for example fragments of a cyclodextrin, starch, chitosan, maltotriose or maltohexaose. The radical —O—G preferably denotes the radical of a mono- or disaccharide or the radical of a cyclodextrin fragment with a maximum of 8 sugar units. Particular preferred saccharide radicals —O—G are the radical of trehalose or the radical of a cyclodextrin fragment. In case that the alkyl radical Y is substituted by a radical —O—($CH_2CH_2O)_{1-24}$—E or —NH—C(O)—O—G wherein —O—G is —O—($CH_2CH_2O)_{1-24}$—E, the number of ($CH_2CH_2O$) units is preferably from 1 to 12 in each case and more preferably from 2 to 8. E is preferably hydrogen or $C_1$–$C_2$-alkyl. Y as $C_5$–$C_8$-cycloalkyl is for example cyclopentyl or preferably cyclohexyl, each of which being unsubstituted or substituted for example by 1 to 3 $C_1$–$C_2$-alkyl groups. Y as $C_7$–$C_{12}$-aralkyl is for example benzyl.

Preferred nonionic radicals —COOY are those wherein Y is $C_1$–$C_4$-alkyl; or $C_2$–$C_4$-alkyl which is substituted by one or two substituents selected from the group consisting of hydroxy; $C_1$–$C_2$-alkoxy; —O—$Si(CH_3)_3$; and —$NR_9R_9'$ wherein $R_9$ and $R_9'$ are each independently of another hydrogen or $C_1$–$C_4$-alkyl; or Y is a radical —$CH_2CH_2$—O—($CH_2CH_2O)_{1-12}$—E wherein E is hydrogen or $C_1$–$C_2$-alkyl; or is a radical —$C_2$–$C_4$-alkylene-NH—C(O)—O—G, wherein —O—G is the radical of a saccharide.

More preferred non-ionic radicals —COOY are those wherein Y is $C_1$–$C_2$-alkyl, particularly methyl; or $C_2$–$C_4$-alkyl which is substituted by one or two substituents selected from the group consisting of —OH and —$NR_9R_9'$ wherein $R_9$ and $R_9'$ are each independently of another hydrogen or $C_1$–$C_2$-alkyl; or a radical —$CH_2CH_2$—O—($CH_2CH_2O)_{1-12}$—E wherein E is hydrogen or $C_1$–$C_2$-alkyl; or is a radical —$C_2$–$C_4$-alkylene-NH—C(O)—O—G wherein —O—G is the radical of a saccharide.

Particularly preferred radicals —COOY comprise those wherein Y is $C_2$–$C_3$-alkyl, which is substituted by hydroxy or N,N-di-$C_1$–$C_2$-alkylamino, or is a radical —$C_2$–$C_3$-alkylene-NH—C(O)—O—G wherein —O—G is the radical of trehalose.

Preferred non-ionic substituents —C(O)—$NY_1Y_2$ of B or B' are those wherein $Y_1$ and $Y_2$ are each independently of the other hydrogen or $C_1$–$C_4$-alkyl which is unsubstituted or substituted by hydroxy; or $Y_1$ and $Y_2$ together with the adjacent N-atom form a heterocyclic 6-membered ring having no further heteroatom or having one further N- or O-atom. Even more preferred meanings of $Y_1$ and $Y_2$ independently of each other, are hydrogen or $C_1$–$C_2$-alkyl which is unsubstituted or substituted by hydroxy; or $Y_1$ and $Y_2$ together with the adjacent N-atom form a N-$C_1$–$C_2$-alkylpiperazino or morpholino ring. Particularly preferred non-ionic radicals —C(O)—$NY_1Y_2$ are those wherein $Y_1$ and $Y_2$ are each independently of the other hydrogen or $C_1$–$C_2$-alkyl; or $Y_1$ and $Y_2$ together with the adjacent N-atom form a morpholino ring.

Preferred non-ionic substituents —$OY_3$ of B or B' are those wherein $Y_3$ is hydrogen, $C_1$–$C_4$-alkyl which is unsubstituted or substituted by —$NH_2$ or —$N(C_1$–$C_2$-alkyl$)_2$, or is a group —$C(O)C_1$–$C_2$-alkyl. $Y_3$ is particularly preferred hydrogen or acetyl.

Preferred non-ionic heterocyclic substituents of B or B' are a 5- or 6-membered heteroaromatic or heteroaliphatic radical having one N-atom and in addition no further heteroatom or an additional N- or O-heteroatom, or is a 5 to 7-membered lactame. Examples of such heterocyclic radicals are N-pyrrolidonyl, 2- or 4-pyridinyl, 2-methyl pyridin-5-yl, 2-, 3- oder 4-hydroxypyridinyl, N-ε-caprolactamyl, N-imidazolyl, 2-methylimidazol-1-yl, N-morpholinyl or 4-N-methylpiperazin-1-yl, particularly N-morpholinyl or N-pyrrolidonyl.

A group of preferred non-ionic substituents of B or B' comprises $C_1$–$C_2$-alkyl, which is unsubstituted or substituted by —OH or —$NR_9R_9'$, wherein $R_9$ and $R_9'$ are each independently of the other hydrogen or $C_1$–$C_2$-alkyl; a radical —COOY wherein Y is $C_1$–$C_4$-alkyl; $C_2$–$C_4$-alkyl which is substituted by —OH or —$NR_9R_9'$ wherein $R_9$ and $R_9'$ are each independently of another hydrogen or $C_1$–$C_2$-alkyl, or Y is a radical —$C_2$–$C_4$-alkylene-NH—C(O)—O—G wherein —O—G is the radical of a saccharide; a radical —C(O)—$NY_1Y_2$, wherein $Y_1$ and $Y_2$ are each independently of the other hydrogen or $C_1$–$C_4$-alkyl which is unsubstituted or substituted by hydroxy, or $Y_1$ and $Y_2$ together with the adjacent N-atom form a heterocyclic 6-membered ring having no further heteroatom or having one further N- or O-atom; a radical —$OY_3$, wherein $Y_3$ is hydrogen, $C_1$–$C_4$-alkyl which is unsubstituted or substituted by —$NH_2$ or —$N(C_1$–$C_2$-alkyl$)_2$, or is a group —C(O)$C_1$–$C_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O—G wherein —O—G is the radical of trehalose; a radical —CO—$NY_1Y_2$, wherein $Y_1$ and $Y_2$ are each independently of the other hydrogen or $C_1$–$C_2$-alkyl which is unsubstituted or substituted by hydroxy, or $Y_1$ and $Y_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3- oder 4-hydroxypyridinyl, N-ε-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —$CONH_2$, —$CON(CH_3)_2$, —CONH—$(CH_2)_2$—OH,

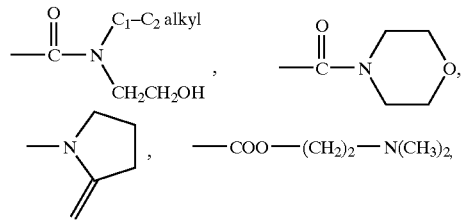

and —COO$(CH_2)_{2-4}$—NHC(O)—O—G wherein —O—G is the radical of trehalose.

Preferred anionic substituents of B or B' are $C_1$–$C_4$-alkyl, in particular $C_1$–$C_2$-alkyl, which is substituted by one or more substituents selected from the group consisting of —$SO_3H$ and —$OPO_3H_2$, for example —$CH_2$—$SO_3H$; phenyl which is substituted by —$SO_3H$ or sulfomethyl, for example o-, m- or p-sulfophenyl or o-, m- or p-sulfomethylphenyl; —COOH; a radical —$COOY_4$, wherein $Y_4$ is $C_2$–$C_6$-alkyl which is substituted by —COOH, —$SO_3H$, —$OSO_3H$, —$OPO_3H_2$, or by a radical —NH—C(O)—O—G' wherein G' is the radical of lactobionic acid, hyaluronic acid or sialic acid, in particular $C_2$–$C_4$-alkyl which is substituted by —$SO_3H$ or —$OSO_3H$; a radical —$CONY_5Y_6$ wherein $Y_5$ is $C_1$–$C_6$-alkyl substituted by sulfo, in particular $C_2$–$C_4$-alkyl substituted by sulfo, and $Y_6$ is hydrogen, for example the radical —C(O)—NH—$C(CH_3)_2$—$CH_2$—$SO_3H$; or —$SO_3H$; or a suitable salt thereof. Particular preferred anionic substituents of B or B' are —COOH, —$SO_3H$, o-, m- or p-sulfophenyl, o-, m- or p-sulfomethylphenyl or a radical —$CONY_5Y_6$ wherein $Y_5$ is $C_2$–$C_4$-alkyl substituted by sulfo, and $Y_6$ is hydrogen, especially carboxy.

(iii) Cationic Substituents:

Preferred cationic substituents of B or B' are $C_1$–$C_4$-alkyl, in particular $C_1$–$C_2$-alkyl, which is in each case substituted by —$NR_9R_9'R_9''^+An^-$; or a radical —$C(O)OY_7$ wherein $Y_7$ is $C_2$–$C_6$-alkyl, in particular $C_2$–$C_4$-alkyl, which is in each case substituted by —$NR_9R_9'R_9''^+An^-$ and is further unsubstituted or substituted by hydroxy. $R_9$, $R_9'$ and $R_9''$ are each independently of another preferably hydrogen or $C_1$–$C_4$-alkyl, more preferably methyl or ethyl and particularly preferably methyl. Examples of suitable anions $An^-$ are $Hal^-$, wherein Hal is halogen, for example $Br^-$, $F^-$, $J^-$ or particularly $Cl^-$, furthermore $HCO_3^-$, $CO_3^{2-}$, $H_2PO_3^-$, $HPO_3^{2-}$, $PO_3^{3-}$, $HSO_4^-$, $SO_4^{2-}$ or the radical of an organic acid such as $OCOCH_3^-$ and the like. A particularly preferred cationic substituent of B or B' is a radical —$C(O)OY_7$ wherein $Y_7$ is $C_2$–$C_4$-alkyl, which is substituted by —$N(C_1$–$C_2$-alkyl$)_3^+An^-$ and is further substituted by hydroxy, and $An^-$ is an anion, for example the radical —C(O)O—$CH_2$—CH(OH)—$CH_2$—$N(CH_3)_3^+An^-$.

(iv) Zwitterionic Substituents —$R_3$—Zw:

$R_3$ is a preferably a carbonyl, ester or amide functional group and more preferably an ester group —C(O)—O—.

Suitable anionic groups of the moiety Zw are for example —$COO^-$, —$SO_3^-$, —$OSO_3^-$, —$OPO_3H^-$ or bivalent —O—$PO_2^-$— or —O—$PO_2^-$—O—, preferably a group —$COO^-$ or —$SO_3^-$ or a bivalent group —O—$PO_2^-$—, and in particular a group —$SO_3^-$.

Suitable cationic groups of the moiety Zw are for example a group —$NR_9R_9'R_9''^+$ or a bivalent group —$NR_9R_9'^+$—, wherein $R_9$, $R_9'$ and $R_9''$ are as defined above, and are each independently of the other, preferably hydrogen or $C_1$–$C_6$-alkyl, preferably hydrogen or $C_1$–$C_4$-alkyl and most preferably each methyl or ethyl.

The moiety Zw is for example $C_2$–$C_{30}$-alkyl, preferably $C_2$–$C_{12}$-alkyl, and more preferably $C_3$–$C_8$-alkyl, which is in each case uninterrupted or interrupted by —O— and substituted or interrupted by one of the above-mentioned anionic and cationic groups each, and, in addition, is further unsubstituted or substituted by a radical —$OY_8$, wherein $Y_8$ is hydrogen or the acyl radical of a carboxylic acid.

$Y_8$ is preferably hydrogen or the acyl radical of a higher fatty acid.

Zw is preferably $C_2$–$C_{12}$-alkyl and even more preferably $C_3$–$C_8$-alkyl which is substituted or interrupted by one of the above-mentioned anionic and cationic groups each, and in addition may be further substituted by a radical —$OY_8$.

A preferred group of zwitter-ionic substituents —$R_3$—Z corresponds to the formula —C(O)O-(alk''')-N($R_9$)$_2^+$-(alk')-An$^-$ or —C(O)O-(alk'')-O—PO$_2^-$-(O)$_{0-1}$-(alk''')-N($R_9$)$_3^+$ wherein $R_9$ is hydrogen or $C_1$–$C_6$-alkyl; An$^-$ is an anionic group —COO$^-$, —SO$_3^-$, —OSO$_3^-$ or —OPO$_3$H$^-$, preferably —COO$^-$ or —SO$_3^-$ and most preferably —SO$_3^-$, alk' is $C_1$–$C_{12}$-alkylene, (alk'') is $C_2$–$C_{24}$-alkylene which is unsubstituted or substituted by a radical —O$Y_8$, $Y_8$ is hydrogen or the acyl radical of a carboxylic acid, and (alk''') is $C_2$–$C_8$-alkylene.

(alk') is preferably $C_2$–$C_8$-alkylene, more preferably $C_2$–$C_6$-alkylene and most preferably $C_2$–$C_4$-alkylene. (alk'') is preferably $C_2$–$C_{12}$-alkylene, more preferably $C_2$–$C_6$-alkylene and particularly preferably $C_2$–$C_3$-alkylene which is in each case unsubstituted or substituted by hydroxy or by a radical —O$Y_8$. (alk''') is preferably $C_2$–$C_4$-alkylene and more preferably $C_2$–$C_3$-alkylene. $R_9$ is hydrogen or $C_1$–$C_4$-alkyl, more preferably methyl or ethyl and particularly preferably methyl. A preferred zwitterionic substituent of B or B' is of formula

—C(O)O—CH$_2$—CH (O$Y_8$)—CH$_2$—O—PO$_2^-$—(CH$_2$)$_2$—N(CH$_3$)$_3^+$, wherein $Y_8$ is hydrogen or the acyl radical of a higher fatty acid.

In one embodiment of the invention one of B and B' may also be the radical of a hydrophobic comonomer which includes especially those customarily used in the manufacture of contact lenses. Suitable hydrophobic vinylic comonomers include, without the list being exhaustive acrylonitrile, methacrylonitrile, vinyl-$C_1$–$C_{18}$-alkanoates, $C_2$–$C_{18}$-alkenes, $C_2$–$C_{18}$-haloalkenes, styrene, $C_1$–$C_6$-alkylstyrene, $C_2$–$C_{10}$-perfluoroalkyl acrylates and methacrylates or correspondingly partially fluorinated acrylates and methacrylates, $C_3$–$C_{12}$-perfluoroalkyl-ethyl-thiocarbonylaminoethyl acrylates and methacrylates, acryloly- and methacryloxy-alkyl-sil-oxanes, N-vinylcarbazole and the like. Examples of suitable hydrophobic vinylic comonomers include acrylonitrile, methacrylonitrile, vinyl acetate, vinyl propionate, vinylbutyrate, vinyl valerate, styrene, chioroprene, vinyl chloride, vinylidene chloride, 1-butene, butadiene, vinyltoluene, perfluorohexylethylthiocarbonylaminoethyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyl disiloxane and bis(methacryloxypropyl)tetramethyldisiloxane.

B denotes for example a radical of formula

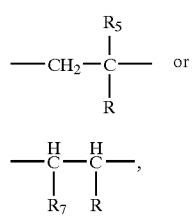

(4a)

(4b)

wherein $R_5$ is hydrogen or $C_1$–$C_4$-alkyl, preferably hydrogen or methyl; $R_6$ is a hydrophilic substituent, wherein the above given meanings and preferences apply; $R_7$ is $C_1$–$C_4$-alkyl, phenyl or a radical —C(O)O$Y_9$, wherein $Y_9$ is hydrogen or unsubstituted or hydroxy-substituted $C_1$–$C_4$-alkyl; and $R_8$ is a radical —C(O)$Y_9$' or —CH$_2$—C(O)O$Y_9$' wherein $Y_9$' independently has the meaning of $Y_9$.

$R_7$ is preferably $C_1$–$C_2$-alkyl, phenyl or a group —C(O)O$Y_9$. $R_8$ is preferably a group —C(O)O$Y_9$' or —CH$_2$—C(O)O$Y_9$' wherein $Y_9$ and $Y_9$' are each independently of the other hydrogen, $C_1$–$C_2$-alkyl or hydroxy-$C_1$–$C_2$-alkyl. Particularly preferred —CH$R_7$—CH$R_8$— units according to the invention are those wherein $R_7$ is methyl or a group —C(O)O$Y_9$ and $R_8$ is a group —C(O)O$Y_9$' or —CH$_2$—C(O)O$Y_9$' wherein $Y_9$ and $Y_9$' are each hydrogen, $C_1$–$C_2$-alkyl or hydroxy-$C_1$–$C_2$-alkyl.

B' independently may have one of the meanings given above for B or is the radical of a hydrophobic comonomer, for example the radical of one of the above-given hydrophobic comonomers.

If (oligomer) is a telomer radical of formula (3a), the radical -(alk)-S—[B]$_p$—[B']$_q$—Q preferably denotes a radical of formula

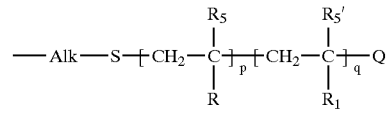

(3a') and even more preferably of the formula

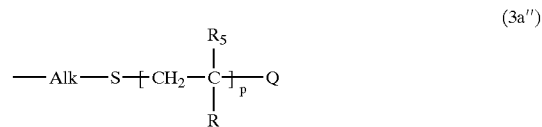

(3a'')

wherein for $R_5$, $R_6$, Q, p and q the above-given meanings and preference apply, for $R_5$' independently the meanings and preferences given before for $R_5$ apply, and for $R_6$' independently the meanings and preferences, given before for $R_6$ apply or $R_6$' is a hydrophobic substituent selected from the group consisting of hydrogen, —CN, $C_1$–$C_{18}$-alkanoyl, $C_1$–$C_{16}$-alkyl. $C_1$–$C_{16}$-haloalkyl, phenyl, $C_1$–$C_6$-alkylphenyl, $C_2$–$C_{10}$-perfluoroalkyloxycarbonyl or a corresponding partially fluorinated alkyloxycarbonyl radical, $C_3$–$C_{12}$-perfluoroalkylethyl-thiocarbonylaminoethyloxycarbonyl, alkylsiloxyloxycarbonyl and carbazolyl.

A preferred group of suitable hydrophilic macromers according to the invention comprises compounds of the above formula (1) wherein R is hydrogen or methyl, $R_1$ is hydrogen, methyl or carboxyl, $R_1$' is hydrogen, A is a radical of the above formula (2a), (2b) or (2e), wherein n and m are each 0 or 1, X and $X_1$ are each independently of the other —O— or —NH—, $A_1$ is unsubstituted or hydroxy-substituted —O—$C_2$–$C_8$-alkylene or a radical —O—$C_2$–$C_6$-alkylene-NH—C(O)—, $A_2$ is $C_1$–$C_4$-alkylene, phenylene or benzylene, (alk*) is $C_2$–$C_4$-alkylene, and (oligomer) denotes a radical of formula

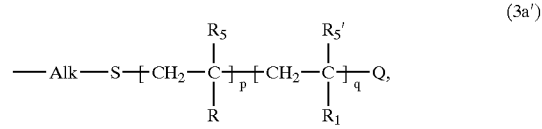

(3a')

wherein (alk) is $C_2$–$C_6$-alkylene, Q is a monovalent group that is suitable to act as a polymerization chain-reaction terminator, p and q are each an integer of from 0 to 100 and the total of (p+q) is from 5 to 100, $R_5$ and $R_5'$ are each independently of the other hydrogen or methyl, and for $R_6$ and $R_6'$ each independently of the other the meanings and preferences given before apply. One particularly preferred embodiment of the above outlined hydrophilic macromers comprises those wherein q is 0, p is from 5 to 100, $R_5$ is hydrogen or methyl, and $R_6$ is a radical —$CONH_2$, —$CON(CH_3)_2$, —$CONH$—$(CH_2)_2$—$OH$,

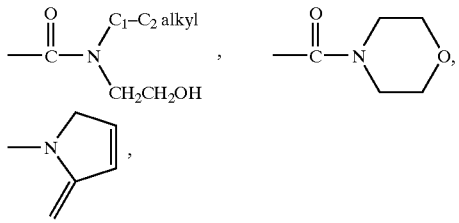

—$COO$—$(CH_2)_2$—$N(CH_3)_2$, or —$COO(CH_2)_{2-4}$—$NHC(O)$—$O$—$G$ wherein —$O$—$G$ is the radical of trehalose. A further preferred embodiment of the above outlined hydrophilic macromers comprises those wherein p is from 4 to 99, q is from 1 to 96 wherein in the total of (p+q) is from 5 to 100, $R_5$ and $R_5'$ are each independently hydrogen or methyl, $R_6$ is a radical —$CONH_2$, —$CON(CH_3)_2$, —$CONH$—$(CH_2)_2$—$OH$,

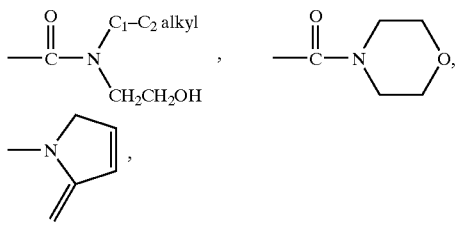

—$COO$—$(CH_2)_2$—$N(CH_3)_2$, or —$COO(CH_2)_{2-4}$—$NHC(O)$—$O$—$G$ wherein —$O$—$G$ is the radical of trehalose, and $R_6'$ independently has the meaning of $R_6$ or is carboxy, subject to the proviso that $R_6$ and $R_6'$ are different.

A more preferred group of suitable hydrophilic macromonomers according to the invention comprises compounds of formula

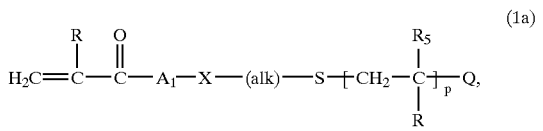

wherein R is hydrogen or methyl, $A_1$ is —O—$(CH_2)_{2-4}$—, —O—$CH_2$—$CH(OH)$—$CH_2$— or a radical —O—$(CH_2)_{2-4}$—NH—C(O)—, X is —O— or —NH—, (alk) is $C_2$–$C_4$-alkylene, Q is a monovalent group that is suitable to act as a polymerization chain-reaction terminator, p is an integer from 5 to 50, $R_5$ is hydrogen or methyl, and for $R_6$ the above given meanings and preferences apply.

A particularly preferred embodiment of the invention relates to hyprophilic macromonomers of the formula

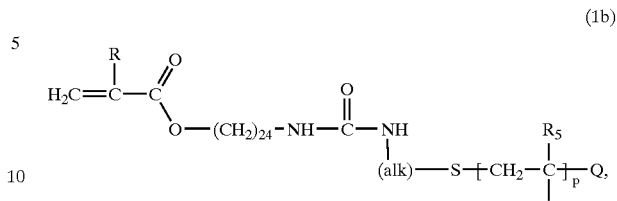

wherein for R, $R_5$, $R_6$, Q, (alk) and p the above-given meanings and preferences apply. A particularly preferred group of hydrophilic macromonomers are compounds of the above formula (Ib) wherein R is hydrogen or methyl, (alk) is $C_2$–$C_4$-alkylene, $R_5$ is hydrogen or methyl, p is an integer of 5 to 50, Q is as defined before, and for $R_6$ the above given meanings and preferences apply.

If (oligomer) is a radical (ii) of formula (3b), Q' in formula (3b) is for example $C_1$–$C_{12}$-alkyl, phenyl or benzyl, preferably $C_1$–$C_2$-alkyl or benzyl and in particular methyl. $R_{29}$ is preferably unsubstituted or hydroxy-substituted $C_1$–$C_4$-alkyl and in particular methyl. u is preferably an integer from 2 to 150, more preferably from 5 to 100, even more preferably from 5 to 75 and particularly preferably from 10 to 50.

If (oligomer) is a radical of formula (3b'), the above given meanings and preferences apply for the variables X, $R_{29}$ and u contained therein.

If (oligomer) denotes a radical (iv) of formula (3c), $R_2$ and $R_2^{1'}$ are each preferably ethyl or in particular methyl; v is preferably an integer from 2 to 150, more preferably from 5 to 100, even more preferably from 5 to 75 and particularly preferably from 10 to 50; Q" is for example hydrogen; and An⁻ is as defined before.

If (oligomer) denotes an oligopeptide radical (v) of formula (3d) or 3d'), $R_4$ is for example hydrogen, methyl, hydroxymethyl, carboxymethyl, 1-hydroxyethyl, 2-carboxyethyl, isopropyl, n-, sec. or iso-butyl, 4-amino-n-butyl, benzyl, p-hydroxybenzyl, imidazolylmethyl, indolylmethyl or a radical —$(CH_2)_3$—NH—C(=NH)—$NH_2$. t is preferably an integer from 2 to 150, more preferably from 5 to 100, even more preferably from 5 to 75 and particularly preferably from 10 to 50.

If (oligomer) denotes a polyoxyalkylene radical (vi) of formula (3e), $R_{30}$ is preferably hydrogen or $C_1$–$C_{18}$-alkyl, more preferably hydrogen or $C_1$–$C_{12}$-alkyl, even more preferably hydrogen, methyl or ethyl, and particularly preferably hydrogen or methyl. (alk**) is preferably a $C_2$–$C_3$-alkylene radical. z is preferably 0. r and s are each independently preferably an integer from 0 to 100 wherein the total of (r+s) is 5 to 100. r and s are each independently more preferably an integer from 0 to 50 wherein the total of (r+s) is 8 to 50. In a particularly preferred embodiment of the polyoxyalkylene radicals (oligomer), r is an integer from 8 to 50 and particularly 9 to 25, and s is 0.

(oligomer) as the radical of an oligosaccharide (vii) may be, for example, a di- or polysaccharide including carbohydrate containing fragments from a biopolymer. Examples are the radical of a cyclodextrin, trehalose, cellobiose, maltotriose, maltohexaose, chitohexaose or a starch, hyaluronic acid, deacetylated hyaluronic acid, chitosan, agarose, chitin 50, amylose, glucan, heparin, xylan, pectin, galactan, glycosaminoglycan, mucin, dextran, aminated dextran, cellulose, hydroxyalkylcellulose or carboxyalkylcellulose oligomer, each of which with a molecular weight average weight of, for example, up to 25000, preferably up to 10000. Preferably the oligosaccharide according to (vii) is the radical of a cyclodextrin with a maximum of 8 sugar units.

In the above formulae (2a), (2b), (2c), (2d) and (2e), the left bond is in each case attached to the double bond whereas the right bond is linked to the oligomer. Formulae (3a), (3a') and (3e) are to be understood as a statistic description of the respective oligomeric radicals, that is to say, the orientation of the monomers and the sequence of the monomers (in case of copolymers) are not fixed in any way by said formulae. The arrangement of B and B' in formula (3a) or of the ethyleneoxide and propyleneoxide units in formula (3e) thus may be random or blockwise. Throughout the whole description, anions such as —COOH or —$SO_3H$ groups always include suitable salt forms, preferably biomedical or especially ophthalmically acceptable salts, in particular —$COO^-Ka^+$ and —$SO_3^-Ka^+$ groups wherein $Ka^+$ is a cation such as an alkali metal cation or an ammonium cation.

The weight average molecular weight of the macromonomers capable of use in the present invention depends principally on the desired properties and is for example from 300 to 50000, preferably from 300 to 12000, more preferably from 300 to 8000, even more preferably 300 to 5000, and particularly preferably from 500 to 2000.

The macromonomers of formula (1) may be prepared by methods, for example as described in WO 99/57581 which has been incorporated herein by reference.

The hydrophilic monomers and macromonomers may be applied to the initiator-modified bulk material surface and polymerized there according to various known processes. For example, the bulk material is immersed in a solution of the monomer or macromonomer, or a layer of monomer or macromonomer is first of all deposited on the modified bulk material surface, for example, by dipping, spraying, spreading, knife coating, pouring, rolling, spin coating or vacuum vapor deposition. The polymerization of the macromonomer on the bulk material surface then may be initiated, for example, thermally by the action of heat or by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend for example on the desired properties of the resulting composite material but is usually in the range of up to 30 minutes, preferably from 10 seconds to 10 minutes, and particularly preferably from 0.5 to 5 minutes. The irradiation may be carried out under ambient conditions or in an atmosphere of an inert gas, for example nitrogen. After the polymerization, any non-covalently bonded polymers, oligomers or non-reacted monomer or macromonomers formed can be removed, for example by treatment with suitable solvents.

The grafting of such macromonomers to the bulk substrate material surface through attachment at the reactive sites of a polymeric tie layer yields a hydrophilic layer having for example a so-called bottle brush-type structure (BBT) composed of tethered "hairy" chains. Such BBT structures in one embodiment comprise a long hydrophilic or hydrophobic backbone which carries relatively densely packed comparatively short hydrophilic side chains (called primary bottle brushes). Another embodiment relates to secondary bottle brushes which are characterized in that the hydrophilic side chains themselves carry densely packed hydrophilic "secondary" side chains. Polymeric coatings of said primary and secondary BBT structures to a certain extent mimic highly water-retaining structures occurring in the human body, for example in cartilage or mucosal tissue.

The coating thickness of the hydrophilic surface coating depends principally on the desired properties. In case of macromonomers, thicknesses can vary from about 0.001 to about 1000 μm, from about 0.01 to about 500 μm, from about 0.01 to about 100 μm, from about 0.05 to about 50 μm, from about 0.1 to about 5 μm, from about 0.1 to about 1 μm, or from about 0.2 to about 0.6 μm.

The complete coating of the bulk material according to the invention consists (a) of at least a partial tie layer, one or more tie layers comprising polyelectrolytes and (b) of outer coating which may be hydrophilic or which may comprise various other active agents such as anti-microbial agents, organoselenium or block-type copolymers wherein one block is LbL active and the other is not. When the outer coating is hydrophilic, it is obtained by grafting one or more hydrophilic monomers or macromonomers onto the surface, wherein the latter makes up at least 50%, from about 75 to about 98% and from about 80 to about 95% of the total thickness of the fully hydrated coating.

Such tie layers are particularly useful on biomedical devices such as ophthalmic devices like contact lenses. Contact lenses, both hard and soft, intraocular lenses and artificial corneas are also particularly useful candidates to receive the tie layers of the present invention. The inventive materials are further useful, for example, as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The biomedical devices such as the coated ophthalmic devices of the present invention exhibit a variety of unexpected advantages over those of the prior art which make those devices very suitable for practical purposes, e.g. as contact lens for extended wear or intraocular lens. For example, such hydrophilic surface-coated lenses have a high surface wettability as demonstrated by their contact angles, good water retention ability and acceptable water-film break up time or tear film break up time.

In addition, biomedical devices such as contact lenses with the present tie layers may exhibit certain desirable mechanical qualities. For example, the devices may be made blood compatible and have a good tissue integration. Moreover, the dimensional stability of the composite materials of the invention is excellent. In addition, the attachment of a hydrophilic surface coating at a given bulk material according to the invention does not affect its visual transparency.

In summary, the ophthalmic devices such as intraocular lenses and artificial cornea or particularly contact lenses, may be formed in accordance with the present invention to provide a combination of low spoilation with respect to cell debris, cosmetics, tear components, lipids, proteins, salts, dust or dirt, solvent vapors or chemicals, with a high comfort for the patient wearing such opthalmic devices in view of the soft hydrogel surface which for example provides a very good on-eye movement of the ophthalmic device.

It is to be further understood that the present invention is not limited to contact lenses. Various biomedical devices such as renal dialysis membranes, blood storage bags, pacemaker leads or vascular grafts made of the composite materials of the invention resist fouling by proteins by virtue of the continuous layer of bound water, thus reducing the rate and extent of thrombosis. Blood-contacting devices fabricated according to the present invention may, therefore, be made haemocompatible and biocompatible.

EXAMPLES

The present invention may be more readily understood by reference to the following Examples, without being limited thereto.

In the following examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Krüss GmbH, Hamburg, Germany). Wetting force on the solid is measured as the solid is immersed in or withdrawn from a liquid of known surface tension.

The molecular weight ("MW") for the polymers utilized is set forth as an approximation. If no molecular weight is given, then the molecular weight is that set forth for the same polymer in the example prior to that particular example.

Example A-1

Preparation of Aminofunctionalized Contact Lenses by Attaching a Tie Layer a.) A 0.001M polyacrylic acid (PAA) solution (MW≈90,000) is prepared by adding 0.29 grams of a 25% aqueous PAA stock solution to 1000 ml of ultra-pure water in a beaker. Then the pH of the solution is adjusted to 2.5 by adding 1N HCl and the solution is filtered using qualitative filter paper.

b.) A 0.001M polyallylamine hydrochloride (PAH) solution (MW≈50,000–65,000) is prepared by adding 0.09 g PAH (solid) into a small beaker; dissolving in ultra-pure (UP) water and transferring into a bigger beaker with a final volume of 1000 ml aqueous solution. The pH is then adjusted to 4.5 as measured with a pH meter. The solution is then filtered using qualitative filter paper.

c.) Swollen non-coated Lotrafilcon a lenses (polysiloxane/perfluoroalkyl polyether copolymer) in isopropanol (IPA) are individually immersed into the solution a.) for 5 minutes. After this time, the lenses are withdrawn from the solution a.) and directly immersed into the solution b.) for additional 5 minutes. The lenses were rinsed with water between the two dips. After this, the lenses are released into UP water and stored at 4° C. for further use.

Example A-2

Preparation of Aminofunctionalized Contact Lenses by Attachment of a Tie Layer a.) A 0.1% by weight solution of a branched polyacrylic acid (Carbopol® 981 NF) is prepared by adding 0.05 g of Carbopol® 981 NF (BFGoodrich) to 50 ml of isopropanol-ultra-pure water mixture (1:4) in a beaker. After complete dissolution (overnight), the pH of the solution is adjusted to 2.5 by adding 1N HCl and the solution is filtered using qualitative filter paper.

b.) 100 ml of 0.05% solution of polyethyleneimine (PEI) is prepared by adding 0.1 g of 50% aqueous PEI stock solution into a mixture of isopropanol-ultra-pure water 1:4. The pH is then adjusted to 3.5 by adding 1N HCl as measured by pH meter. The solution is then filtered using qualitative filter paper.

c.) Swollen non-coated Lotrafilcon a lenses in isopropanol (IPA) are individually immersed into the solution a.) for 10 minutes. The lenses are withdrawn from the solution a.) rinsed with ultra-pure water and immersed into the solution b.) for additional 10 minutes. After this, the lenses are released into ultra-pure water and stored at 4° C. for further use.

Example B-1

Surface Binding of Reactive Photoinitiator Molecules

The aminofunctionalized contact lenses from Example A-1 are first immersed into acetonitrile for 1 hour (20 ml acetonitrile/lens). The lenses are then withdrawn and directly immersed into a 1% by weight solution of the reactive photoinitiator prepared by the addition reaction from isophorone diisocyanate and 4-(2-hydroxyethoxy)phenyl 2-hydroxy-2-propyl ketone (Darocure 2959) (synthesis see EP 0 632 329) in acetonitrile. 3 drops of triethylamine (TEA) are then added to the solution. The amino groups on the lens surface react with the isocyanato groups of the photoinitiator molecules for 12 hours. After this time, the lenses are withdrawn from the reaction solution, washed three times, and extracted in acetonitrile for 8 hours and dried under reduced pressure for 2 hours. The dried lenses are subsequently used for photografting.

Example B-2

Surface Binding of the Reactive Photoinitiator Molecules

The aminofunctionalized contact lenses from Example A-2 are dried to the constant mass under reduced pressure. The lenses are then directly immersed into 1% by weight acetonitrile solution of the reactive photoinitiator prepared by the addition reaction from isophorone diisocyanate and 2-dimethylamino-2-benzyl-1-[4-(2-hydroxyethoxy)phenyl]-butan-1-one (synthesis see WO 96/20796(20 ml solution/lens). 3 drops of triethylamine (TEA) are then added to the solution. The amino groups on the lens surface react with the isocyanato groups of the photoinitiator molecules for 12 hours. After this time, the lenses are withdrawn from the reaction solution, washed 3 times, and extracted in acetonitrile for 6 hours and dried under reduced pressure for 2 hours. The dried lenses are subsequently used for photografting.

Example C-1

Acrylamide Telomer (MW=2000) Synthesis

A 1000 mL round bottom flask is charged with a solution of 71.1 g (1 mol) Acrylamide, 4.93 g (18.2 mmol) α,α'-azodiisobutyramidine dihydrochloride and 4.93 g (36.4 mmol) cysteaminhydrochloride in 400 ml of water. The clear and slightly yellowish solution is acidified with a few drops of hydrochloric acid to pH3. The stirred acidic solution is evacuated to 50 mbar and filled with argon. This is repeated three times. With a constant stream of Argon, this solution is poured into a 500 ml dropping funnel which is put onto an 'flow-through-reactor' consisting of an 1000 ml three-necked round-bottom flask, reflux condenser, thermometer, magnetic stirrer and a 30 cm Liebig-condenser, which is filled with glass wool. The whole apparatus is constantly purged with argon. The dropping funnel is put onto the Liebig condenser, which is heated to 65° C. The flask is heated to 60° C. The solution is slowly dropped through the Liebig-condenser into the stirred flask. This takes 2.5 hours. During this time the temperature in the flask is kept between 58–65° C. After the completed addition, the solution is stirred for 2 hours at 60° C.

NaOH is added to the clear and slightly yellowish solution until pH 10 is reached. The product is purified through reverse osmosis, using Millipore cartridge with a cut-off at 1000 Da and freeze-dried. A bright-white solid product is obtained ($NH_2$ 0.34 mEq/g sulfur-value of the elemental analysis (0.33 mEq/g); Mn 2000 g/Mol).

Example C-2

Acrylamide Telomer (MW=1350) Synthesis

A 1000 mL round bottom flask is charged with a solution of 99.5 g (1.46 mol) acrylamide, 1.27 g (4.68 mmol) α,α'-azodiisobutyramidine dihydrochloride and 15.9 g (0.14 mol) cysteaminhydrochloride in 300 ml of water. The clear and slightly yellowish solution is acidified with a few drops of hydrochloric acid (32%) to pH 3. The stirred acidic solution is evacuated to 50 mbar and filled with argon. This is repeated three times. With a constant stream of argon, this solution is poured into a 500 ml dropping funnel which is put onto an 'flow-through-reactor' consisting of an 1000 ml three-necked round-bottom flask, reflux condenser, thermometer, magnetic stirrer and a 30 cm Liebig-condenser, which is filled with glass wool. The whole apparatus is constantly purged with argon. The dropping funnel is put onto the Liebig condenser, which is heated to 65° C. The flask is heated to 60° C. The solution is slowly dropped through the Liebig-condenser into the stirred flask. This takes 2 hours. During this time the temperature in the flask is kept between 58–65° C. After the completed addition, the solution is stirred for 2 hours at 60° C.

NaOH is added to the clear and slightly yellowish solution until pH 10 is reached. The product is purified through reverse osmosis, using Millipore cartridge with a cut-off at 1000 Da and then freeze-dried for 18 hours. A bright-white solid product is obtained ($NH_2$ 0.70 mEq/g, sulfur-value of the elemental analysis (0.73mEq/g; MW=1350g/Mol).

Example C-3

N,N-dimethyl Acrylamide Telomer (MW=1850) Synthesis

A 2000 mL round bottom flask is charged with a solution of 198.2 g (2 mol) N,N-dimethyl acrylamide, 2.72 g (10 mmol) α,α'-azodiisobutyramidine dihydrochloride and 24.8 g (0.22 mol) cysteaminhydrochloride in 600 ml of water. The clear and slightly yellowish solution is acidified with a few drops of Hydrochloric Acid (32%), pH of 3. The stirred acidic solution is evacuated to 50 mbar and filled with argon. This is repeated three times. With a constant stream of argon, this solution is poured into a 1000 ml dropping funnel which is put onto an 'flow-through-reactor' consisting of an 1000 ml three-necked round-bottom flask, reflux condenser, thermometer, magnetic stirrer and a 30 cm Liebig-condenser, which is filled with glass wool. The whole apparatus is constantly purged with argon.

The dropping funnel is put onto the Liebig condenser, which is heated to 60° C. The flask is also heated to 60° C. The solution is slowly dropped through the Liebig-condenser into the stirred flask. This takes 2.5 hours. During this time the temperature in the flask is kept between 58–65° C. After the completed addition, the solution is stirred for 2 hours at 60° C. 30% NaOH solution is added to the clear and slightly yellowish solution until pH 10 is reached. The product is purified through reverse osmosis, using Millipore cartridge with a cut-off at 1000 Da and freeze-dried. A bright-white solid product is obtained ($NH_2$ 0.54mEq/g; MW=~1850 g/Mol).

Example D-1

Preparation of IEM-functionalized Acrylamide Telomer Solution 7.5 g of acrylamide telomer with amino end group (amine titration=0.70 mEq/g), prepared by Example C-2 are dissolved in 80 ml of HPLC water. Argon is then let to bubble through the solution for the period of about 30 minutes. This mixture is then added to the equimolar amount (0.81 g) of isocyanatoethyl methacrylate (IEM, isocyanate titration=6.45 mEq/g) under stirring. The whole mixture is then stirred under argon flow for 12 hours. After adding of 0.8 g of NaCl to the solution and 10 minutes stirring, the mixture is filtered through 0.45 μm Teflon filter, degassed by repeated (3 times) evacuation and bubbling with argon in order to remove oxygen and used for photografting.

Example D-2

Preparation of IEM-functionalized N,N-dimethylacrylamide Telomer Solution 5 g of N,N-dimethylacrylamide telomer with amino end group (amine titration=0.53 mEq/g), prepared by Example C-3 are dissolved in 100 ml of HPLC water. Argon is then let to bubble through the solution for the period of about 30 minutes. This mixture is then added to the equimolar amount (0.41 g) of isocyanatoethyl methacrylate (IEM, isocyanate titration=6.45 mEq/g) under stirring. The whole mixture is then stirred under argon flow for 12 hours. After adding of 1.0 g of NaCl to the solution and 10 minutes stirring, the mixture is filtered through 0.45 μm Teflon filter, degassed with nitrogen in order to remove oxygen and used for photografting.

Example E-1

Photografting of IEM-functionalized Acrylamide Telomers onto a Contact Lens Surface 1 ml of the IEM-functionalized acrylamide telomer solution from Example D-1 is introduced into a small Petri dish of a volume of about 2 ml in a glove box. The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 14.5 $mW/cm^2$ ultraviolet light for a period of about 1.5 minutes.

The modified lens is then withdrawn from the solution, washed twice in distilled water, continuously extracted in ultra pure water for 16 hours and analyzed by atomic force microscopy ("AFM"), Fourier Transform Infrared-Attenuated Total Reflection Mode ("ATR-FTIR") and contact angle measurements. The thickness of the coating is in the range of 250–300 nm as determined by AFM.

Water/air contact angles on the modified lens are 0° advancing ("adv.") and 0° receiving ("rec."). In comparison, the contact angles of non-modified lens are 101° adv. and 64° rec. The lens held continuous water layer on the surface for over 1 minute.

Example E-2

Photografting of IEM-functionalized Acrylamide Telomers onto a Contact Lens Surface Two lenses from Example B-1 are coated in accordance with Example E-1, but instead of 1.5 minutes of UV exposure, 1.7 minutes exposition time is used for photografting.

Water/air contact angles on the modified lenses are 0° adv. and 0° rec.

Example E-3

Photografting of IEM-functionalized N,N-dimethylacrylamide Telomers onto a Contact Lens Surface 1 ml of the IEM-functionalized N,N-dimethylacrylamide telomer solution from Example D-2 is introduced into a small Petri dish of a volume of about 2 ml in a glove box. The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 14.5 mW/cm$^2$ ultraviolet light for a period of about 1.5 minutes. The lens is then turned over and the exposition is repeated by applying 14.5 mW/cm$^2$ UV light for an additional 1.5 minutes.

The modified lens is then withdrawn from the solution, washed twice in distilled water, continuously extracted in ultra pure water for 16 hours and analyzed. The thickness of the coating is in the range of 300–400 nm as determined by AFM.

Water/air contact angles on the modified lens are 0° adv. and 0° rec. In comparison, the contact angles of a non-modified lens are 101° adv. and 64° rec.

Example E-4

Photografting of IEM-functionalized Acrylamide Telomers onto the Contact Lens Surface Under Ambient Conditions In a laminar flow hood, 1 ml of the IEM-functionalized acrylamide telomer solution from Example D-1 is introduced into a small Petri dish of a volume of about 2 ml. The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 2.05 mW/cm$^2$ ultraviolet light (MACAM-UV-Lamp) for a period of 2.5 minutes. The modified lens is then withdrawn from the solution, washed twice in distilled water, continuously extracted in ultra pure water for 16 hours and analyzed.

The thickness of the coating is in the range of 500–600 nm as determined by AFM.

Water/air contact angles on the modified lens are 0° adv. and 0° rec. In comparison, the contact angles of non-modified lenses are 101° adv. and 64° rec. The lens held a continuous water layer on the surface for over 1 minute after withdrawing the lens from a saline solution and from water.

Example E-5

Photografting of IEM-functionalized N,N-dimethylacrylamide Telomers onto the Contact Lens Surface Under Ambient Conditions In a laminar flow hood, 1 ml of the IEM-functionalized N,N-dimethylacrylamide telomer solution from Example D-2 is introduced into a small Petri dish of a volume of about 2 ml. The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 2.36 mW/cm$^2$ ultraviolet light (MACAM-UV-Lamp) for a period of 2.5 minutes. The modified lens is then withdrawn from the solution, washed twice in distilled water, continuously extracted in ultra pure water for 16 hours and analyzed.

Water/air contact angles on the modified lens are 6° adv. and 0° rec. In comparison, the contact angles of non-modified lens are 101° adv. and 64° rec.

Example E-6

Photografting of IEM-functionalized Acrylamide Telomers onto the Contact Lens Surface 1 ml of the IEM-functionalized acrylamide telomer solution from Example D-1 is introduced into a small Petri dish of a volume of about 2.5 ml in a glove box. The dried lens from Example B-2, carrying covalently linked photoinitiator molecules on its surface, is then placed into this solution and an additional 1 ml of the degassed solution is added on the lens in order to cover the whole lens with the solution. After 10 minutes, the Petri dish with the lens in the solution is exposed to 14.5 mW/cm$^2$ ultraviolet light for a period of about 3 minutes.

The modified lens is then withdrawn from the solution, washed twice in distilled water, continuously extracted in ultra pure water for 16 hours and analyzed.

Water/air contact angles on the modified lens are 24° adv. and 16° rec. In comparison, the contact angles of non-modified lens are 101° adv. and 64° rec.

Example F

Contact Angles and Sudan Black Staining of Functionalized Lotrafilcon a Contact Lens Surfaces The following tables represent contact angle and Sudan black staining results for Lotrafilcon A contact lens surfaces that were functionalized with various tie layers. The tie layer was applied as set forth hereinabove by either dipping into successive single component polyelectrolyte solutions (Table 1) or into a multi-component single solution (Table 2). The tables list the Modification Condition, the Contact Angle, and the Sudan black staining characteristic on a 0 to 5 scale (with 0 meaning clear, not stained and 5 meaning blue, fully stained). The contact angles for these examples were measured using an automated VCA 2500 contact angle instrument (available from Advanced Surface Technologies of Boston, Mass.) using water as the probe solvent. Sudan black staining analysis was conducted by immersing the lenes into a 1% Sudan black B /Vitamin E solution for 5 minutes. The lenses were then taken out of the Sudan black solution and flushed with tap water. The lenses were then visually inspected to determine if the lenses were clear or stained. If the lenses picked up the stain, there was no tie layer present, or the tie layer was incomplete across the lens surface. An indication of "clear" (no-staining) indicates the presence of one or multiple tie layers on the lens surface.

Table 1 indicates application of the functionalized polymeric tie layer(s) by sequential, single component dipping and Table 2 indicates application of the functionalized polymer tie layer(s) by dipping into multi-component solutions. For the examples in Table 1, the molecular weight of the PEI was approximately 70,000; the molecular weight of the PAH was approximately 50,000 to 65,000; the molecular weight for the PAA used in examples F2, F5, F6, and F7 was approximately 90,000; and the molecular weight for the PAA used in examples F8 and F9 was approximately 250,000. In Table 2, the molecular weight of the PAA used in examples F9, F10, F11, F27, and F28 was approximately 90,000; the molecular weight of the PAA used in examples F12 and F13 was approximately 250,000; the molecular weight of the PAA used in examples F14 and F15 was approximately 750,000; the molecular weight of the PAA used in examples F16 and F17 was approximately 1,000,000; the molecular weight of the PAH used in examples F9–F29 was approximately 50,000–65,000; the molecular weight of the PSSS used in examples F18, F19, F22, and F23 was approximately 500,000; the molecular weight of the PEG used in example F20 was approximately 5,000; and the molecular weight of the PEI used in examples F24 and F25 was approximately 750,000.

TABLE 1

| Sample | Modification Condition | pH | Contact Angle | Sudan Black Staining |
|---|---|---|---|---|
| F1 | Plasma treatment (control) | N/A | 40 ± 6.6 | Clear |
| F2 | IPA/(PAA/PAH) | 2.5 | 0 | Clear |
| F3 | IPA/PAH | N/A | 102 ± 6.4 | N/A |
| F4 | IPA/PEI | N/A | 102 ± 2.3 | N/A |
| F5 | IPA/PEI/PAA | 3.5 | 86 ± 3.5 | N/A |
| F6 | IPA/PEI/PAA/PAH | 2.5 | 33 ± 7.1 | N/A |
| F7 | IPA/PEI/PAA/PAH | 3.5 | 73 ± 3.9 | N/A |
| F8 | IPA/PEI/(PAA/PAH) | 2.5 | 54 ± 3.0 | N/A |
| F9 | IPA/PEI/(PAA/PAH) | 3.5 | 87 ± 15.5 | N/A |

TABLE 2

| Sample | Modification Condition | pH | Contact Angle | Sudan Black Staining |
|---|---|---|---|---|
| F9 | PAA(0.002M)/PAH (0.001M), 10/1 | 3.9 | 99 ± 11 | 4 |
| F10 | PAA(0.002M)/PAH (0.001M), 10/1 | 2.5 | 0 to 70 | 0 (Clear) |
| F11 | PAA(0.001M)/PAH (0.001M), 10/1 | 2.5 | 0 to 70 | 0 |
| F12 | PAA(0.001M)/PAH (0.001M), 10/1 | 3.9 | 106 ± 4 | 4 |
| F13 | PAA(0.001M)/PAH (0.001M), 10/1 | 2.5 | 0 to 70 | 0 |
| F14 | PAA(0.001M)/PAH (0.001M), 20/1 | 4.3 | 100 ± 12 | 4 |
| F15 | PAA(0.001M)/PAH (0.001M), 20/1 | 3.0 | 52 ± 26 | 1.5 |
| F16 | PAA(0.001M)/PAH (0.001M), 20/1 | 3.9 | 93 ± 13 | 3 |
| F17 | PAA(0.001M)/PAH (0.001M), 20/1 | 3.0 | 103 ± 14 | 2 |
| F18 | PSSS(0.001M)/PAH (0.001M), 10/1 | 7.2 | 108 ± 7 | 4 |
| F19 | PSSS(0.001M)/PAH (0.001M), 10/1 | 2.5 | 103 ± 8 | 4 |
| F20 | PEG(1 g/100 ml) | ~6 | 87 ± 10 | 4.5 |
| F21 | PAAm(1 g/100 ml) | ~6 | 101 ± 8 | 4.5 |
| F22 | PSSS(0.01M) | ~10 | 113 ± 1 | 4 |
| F23 | PSSS(0.01M) | 2.5 | 104 ± 5 | 4 |
| F24 | PEI(0.01M) | ~10 | 104 ± 6 | 4 |
| F25 | PEI(0.01M) | 3.5 | 100 ± 2 | 4 |
| F26 | PAH(0.01M) | 4.0 | 77 ± 13 | 4 |

TABLE 2-continued

| Sample | Modification Condition | pH | Contact Angle | Sudan Black Staining |
|---|---|---|---|---|
| F27 | PAA(0.01M) | ~4 | 60 ± 29 | 2.5 |
| F28 | PAA(0.01M) | 2.5 | 33 ± 3 | 0 (Clear, Best) |
| F29 | Control | N/A | 110 ± 4 | 5 (Stained Fully, Worst) |

Example G

Functionalized Lotrafilcon a Contact Lenses with TEMPO Active Agent Outer Surface In accordance with the present process, 2,2,6,6-tetramethyl-1-piperidinyloxy ("TEMPO") was attached as an active agent to the polymeric tie layers bound to the surfaces of Lotrafilcon A contact lenses. TEMPO can be used as a spin label for electronic spin resonance spectroscopy ("ESR"). TEMPO was bound to the polymeric tie layers as was the telomer of Example E-1.

Table 4 shows contact angles of functionalized lotrafilcon A lenses after being stored in water and/or autoclaved. Table 5 shows the results for functionalized lotrafilcon A lenses with TEMPO attached as described in Example E-1. The data in Table 5 reflects amino group density as measured by ESR.

Table 3 shows a comparative control process wherein the contact lenses were functionalized according to conventional plasma treatment processes. For all the coatings, an advancing angle and a receding angle was measured as described above with respect to Examples E. The molecular weight of the PAA used in Examples G was approximately 90,000; and the molecular weight of the PAH used was approximately 50,000–65,000.

TABLE 3

| Sample | Modification Condition | Advancing Angle | Receding Angle |
|---|---|---|---|
| G1 | IPA/PAA/PAH, 2 dips | 32 | 24 |
| G2 | G-1, after pH 10 treatment | 45 | 39 |
| G3 | G-1, after pH 8 treatment | 48 | 34 |
| G4 | G-1, in CH$_3$CN and then H$_2$O | 39 | 33 |

TABLE 4

| Sample | Modification Condition | Advancing Angle | Receding Angle |
|---|---|---|---|
| G5 | IPA/PAA/PAH, 2 dips of alternating PAA and PAH, after 48 hours. in water, before autoclave | 32 | 24 |
| G6 | IPA/PAA/PAH, 2 dips of alternating PAA and PAH, after 48 hours. in water, then autoclaved | 45 | 16 |
| G7 | IPA/PAA/PAH, 9 dips of alternating PAA and PAH, before autoclave | 27.7 | 0 |

TABLE 4-continued

| Sample | Modification Condition | Advancing Angle | Receding Angle |
|---|---|---|---|
| G8 | IPA/PAA/PAH, 9 dips of alternating PAA and PAH, after autoclave | 25 | 0 |
| G9 | IPA/PAA/PAH, 7 dips of alternating PAA and PAH, after autoclave | 14 | 0 |

TABLE 5

| Sample | Modification Condition | Amino Group Density (per $nm^2$ surface area) |
|---|---|---|
| G10 | IPA/PAA/PAH, after treatment with NaOH (pH = 10) | 5.48 |
| G11 | IPA/PAA/PAH, after treatment with NaOH (pH = 8) | 6.31 |
| G12 | IPA/PAA/PAH, after treatment with $Et_3N$ | 7.42 |

Example H

LbL Functionalization for Creating Thick PAAm Tie Layers a) IPA-swollen Lotrafilcon a contact lenses were dipped into a 0.13% PAA solution (MW of 90,000, pH of 2.5 by addition of HCl). The lenses were then extracted into acetonitrile, treated with isocyanatoethyl methacrylate (IEM) and then extracted back into water. The lens surface was placed into a 5% acrylamide monomer solution which was polymerized as described herein and then washed overnight.

b) A branched version of the PAAm-coated lens was then made by initially polymerizing with a 10% acrylic acid/90% acrylamide solution. The lenses were then retreated with IEM and then polymerized with acrylamide alone.

The resulting coated lenses were both highly lubricious and did not take up Sudan black staining and did not attract dust. These coatings proved to be abrasion resistant and, after finger rubbing and rewashing, appeared to be uniformly wettable and cleaning. After autoclaving twice for 30 minutes each time, the lenses retained their properties. Autoclaving is a standard means of sterilizing water-containing (hydrogel) contact lenses. Because all hydrogel lenses must be sterilized, these results indicate that the tie layers are present and that the resultant surface coating/modification is stable to such extremes.

Example I

Swell Dip PAA/PAH Activated Lenses

IPA-swollen contact lenses were dipped into a bicomponent solution of PAA/PAH solution (0.07% PAA with MW of 90,000 and 8.5 ppm of PAH having a MW of 50,000 to 65,000). The lenses were then water-rinsed and extracted into acetonitrile. IEM (2 pipette drops per lens) was used to attach the acrylate groups to the reactive polymeric layer. After extraction back into water, the lenses were placed into the 5% acrylamide solution described above in Example H and polymerized at 35° C. with nitrogen purging. After 45 minutes, the lenses were washed in water overnight and the coating was evaluated.

A lubricious coating that was resistant Sudan black staining was produced. These characteristics did not change after two 30-minute autoclavings. These lenses withstood some finger rubbing abrasion. In addition, a branched version was made by co-polymerizing acrylic acid (10%) with acrylamide and then washing and extracting into acetonitrile and then reattaching IEM to the acrylic acid groups. After extraction into water, a second polymerization with acrylamide was performed, resulting in a branched polyacrylamide structure.

Example J

Swell Dipped PAA/PEI Activated Lenses

IPA-swollen lenses were dipped into a 0.13% PAA solution (MW of 90,000, pH of 2.5 adjusted by HCl addition). After five minutes, the lenses were water-rinsed and then dipped into a 0.044% PEI solution (MW of 70,000, pH of 3.5 adjusted by HCl addition). The lenses were then washed and extracted into acetonitrile, treated with isocyanatoethyl methacrylate (IEM) and then extracted back into water. The lens surface was placed into a 5% acrylamide monomer solution and then polymerized as described above in Example H. Nitrogen purging was performed and sodium persulphate was added at a rate of 40 milligrams per 20 milliliters of solution. The lenses were heated at 35° C. for 45 minutes. After this time, a viscous solution had formed and the lenses were removed by washing in excess water.

After overnight washing in water, the lenses were found to be lubricious to the touch and resistant to Sudan black staining. After autoclaving, the lenses continued to resist Sudan black staining and remained lubricious.

Example K

Organoselenium Attachment to Lenses

Contact lenses having organoselenium as a bioactive agent attached to surfaces modified with functional groups were made as follows. Lotrafilcon A contact lenses were successively dipped into solutions of PAA (pH=3.5) and PAH (pH=7.5) four times as described above. The coated lenses were then activated by soaking them in a 1 milliliter solution comprising EDC (1-(3-dimethylaminopropyl)-3-ethylcarbodiimide hydrochloride) (5 mg), sulfo-NHS (sulfo-N-hydroxysuccinimide) (12 mg) and ultrapure water (10 ml) for 30 minutes. The activated lenses were then soaked overnight in a selenocystamine solution (3 mg/ml water) having a pH of 8.0.

Bioactivity of these functionalized lenses was then tested against *Staphylococcus aureus*. The lenses were suspended in $1 \times 10^4$ of *S. aureus* in PBS (phosphate buffered saline) supplemented with glutathione (0.4 mg/ml) for 24 hours at 37° C. The lenses were then rinsed 5 times in PBS, sonicated and vortexed for 1 minute each into 1 ml of PBS. Dilutions were then prepared and aliquots were plated out for counting.

The number of viable organisms counted for the coated lenses prior to activation and attachment of organoselenium was $67 \times 10^4$. The number of viable organisms counted for lenses that were not coated yet were soaked in the 3 mg/ml selenocystamine as a control was $64 \times 10^2$. The number for the LbL-coated, functionalized, and organoselenium-attached lenses as described was $16 \times 10^2$.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A method for modifying the surface of an article, said method comprising the steps of:
   a) depositing at least a polyelectrolytic tie layer onto the surface of said article, wherein said polyelectrolytic tie layer is composed of (i) one layer of a first polyionic material which is adsorbed onto, heteropolarly bound onto, and/or entraped on the surface of the article or (ii) at least one layer of the first polyionic material which is adsorbed onto, heteropolarly bound onto, and/or entraped on the surface of the article and at least one layer of a second polyionic material having charges opposite of the charges of the first polyionic material, wherein said first and second polyionic materials have functional group which provide reactive sites; and
   b) covalently linking a layer of an active agent to said reactive sites, wherein the active agent is an antimicrobial agent or a polymerization initiator capable of initiating a radical polymerization of ethylenically unsaturated compounds.

2. The method of claim 1 wherein, in the step of depositing, two or more polyelectrolytic tie layers are successively deposited onto said article surface.

3. The method of claim 1 wherein, in the step of depositing, one polyelectrolytic tie layer is deposited onto said article surface.

4. The method of claim 1 wherein said polyelectrolytic tie layer is deposited onto said article surface by contacting said article with one or more polyionic material solutions.

5. The method of claim 4 wherein said layer is deposited by dipping said article into a first solution comprising the first polyionic material having positive or negative charges, removing said article from said first solution, dipping said article into a second solution comprising the second polyionic material having charges that are opposite of the charges of the first polyionic material, and removing said article from said second solution.

6. The method of claim 4 wherein said polyelectrolytic tie layer is deposited onto said article surface by dipping said article into a solution comprising the first polyionic material and the second polyionic material and then removing said article from said solution.

7. The method of claim 4 wherein said contacting occurs by spraying a solution onto the medical device.

8. The method of claim 7 wherein said polyelectrolytic tie layer is deposited by spraying said article with a first solution comprising the first polyionic material having positive or negative charges and then spraying said article with a second solution comprising the second polyionic material having charges opposite of the charges of the first polyionic material.

9. The method of claim 7 wherein said polyelectrolytic tie layer is deposited onto said article surface by spraying said article with a solution comprising the first polyionic material and the second polyionic material.

10. The method of claim 1 wherein said article is a biomedical device.

11. The method of claim 10 wherein said biomedical device is a contact lens.

12. The method of claim 1 wherein said polyelectrolytic layer is deposited onto said article surface by spin-coating said article.

13. The method of claim 1 wherein said polyelectrolytic tie layer is deposited onto said article surface by vapor deposition.

14. The method of claim 4, wherein said polyelectrolytic tie layer is deposited onto the surface of said article by: (1) spraying said article with a first solution comprising the first polyionic material and then dipping said article into a second solution comprising the second polyionic material having charges opposite of the changes of the first polyionic material; or (2) dipping said article into the first solution comprising the first polyionic material and then spraying said article with the second solution comprising the second polyionic material having charges opposite of the charges of the first polyionic material.

15. The method of claim 1, wherein the active agent is a polymerization initiator capable of initiating a radical polymerization of ethylenically unsaturated compounds, and wherein the method further comprises the steps of: (c) contacting the initiator-modified article with a solution of a hydrophilic monomer or macromer; and (d) graft-polymerizing the hydrophilic monomer or macromer onto on the surface of the article.

16. The method of claim 15, wherein the step (c) is carried out by immersing the article in the solution or depositing a layer of the hydrophilic monomer or macromer on the initiator-modified article surface by dipping, spraying, spreading, knife coating, pouring, rolling, spin coating, or vacuum vapor depositing technique.

17. The method of claim 16, wherein the solution is a solution of a hydrophilic monomer selected from the group consisting of hydroxy-substituted $C_2$–$C_4$-alkyl acrylate, hydroxy-substituted $C_2$–$C_4$-alkyl methacrylate, acrylamide, methacrylamide, N,N-di-$C_1$–$C_4$-alkyl acrylamide, N,N-di-$C_1$–$C_4$-alkyl methacrylamide, hydroxy-substituted $C_2$–$C_4$-alkyl acrylamide, hydroxy-substituted $C_2$–$C_4$-alkyl methacrylamide, hydroxy-substituted $C_1$–$C_4$-alkyl vinyl ether, 2-acrylamido-2-methylpropanesulfonic acid, N-vinylpyrrole, N-vinylsuccinimide N-vinylpyrrolidone, 2-vinylpyridine, 4-vinylpyridine, acrylic acid, methacrylic acid, mono-$C_1$–$C_4$-alkylamino-$C_1$–$C_4$-alkyl acrylate, mono-$C_1$–$C_4$-alkylamino-$C_1$–$C_4$-alkyl methacrylate, di-$C_1$–$C_4$-alkylamino-$C_1$–$C_4$-alkyl acrylate, di-$C_1$–$C_4$-alkylamino-$C_1$–$C_4$-alkyl methacrylates, and allylalcohol.

18. The method of claim 16, wherein the solution is a solution of a hydrophilic macromer.

19. The method of claim 1, wherein the active agent is an antimicrobial agent having a functional group capable of reacting with the functional groups of the first polyionic material and/or the second polyionic material.

* * * * *